（12）United States Patent
Gad et al.

(10) Patent No.: US 11,759,403 B2
(45) Date of Patent: Sep. 19, 2023

(54) DOUBLE-LAYERED DENTURE COMPRISING NANOPARTICLES

(71) Applicant: Imam Abdulrahman Bin Faisal University, Dammam (SA)

(72) Inventors: Mohammed Moustafa Ahmed Gad, Dammam (SA); Reem Abualsaud, Dammam (SA); Ahmed Mohamed Rahoma, Dammam (SA); Shaimaa Mohamed Said Fouda, Dammam (SA); Ahmad M. Al-Thobity, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 386 days.

(21) Appl. No.: 17/115,237

(22) Filed: Dec. 8, 2020

(65) Prior Publication Data

US 2022/0175622 A1    Jun. 9, 2022

(51) Int. Cl.
| | |
|---|---|
| *A61K 6/70* | (2020.01) |
| *A61C 8/00* | (2006.01) |
| *A61K 6/17* | (2020.01) |
| *A61K 6/891* | (2020.01) |
| *C08L 33/10* | (2006.01) |
| *C08K 3/08* | (2006.01) |
| *C08K 3/22* | (2006.01) |
| *C08K 3/015* | (2018.01) |
| *B82Y 5/00* | (2011.01) |

(52) U.S. Cl.
CPC .............. *A61K 6/70* (2020.01); *A61C 8/0013* (2013.01); *A61C 8/0095* (2013.01); *A61K 6/17* (2020.01); *A61K 6/891* (2020.01); *C08K 3/015* (2018.01); *C08K 3/08* (2013.01); *C08K 3/22* (2013.01); *C08L 33/10* (2013.01); *B82Y 5/00* (2013.01); *C08K 2003/0806* (2013.01); *C08K 2003/2244* (2013.01); *C08K 2201/011* (2013.01)

(58) Field of Classification Search
CPC ....................................................... A61K 6/70
See application file for complete search history.

(56) References Cited

U.S. PATENT DOCUMENTS

| | | | |
|---|---|---|---|
| 9,675,529 B2 | 6/2017 | Abuelyaman et al. | |
| 10,076,471 B2 | 9/2018 | Nawasrah | |
| 2007/0213460 A1* | 9/2007 | Ruppert ................... | A61K 6/20 |
| | | | 525/14 |

(Continued)

OTHER PUBLICATIONS

Major Base 20 SDS, Major Perodotti Dentari S.P.A., Jun. 25, 2019 (Year: 2019).*

(Continued)

*Primary Examiner* — Michael F Pepitone
(74) *Attorney, Agent, or Firm* — Oblon, McClelland, Maier & Neustadt, L.L.P.

(57) ABSTRACT

Base material arrangements having at least two layers can accommodate the addition of antifungal material (nanofiller), such as in denture base resin without significantly compromising the mechanical properties and/or translucency of the base material arrangements. Antifungal agents such as nanosilver and nanozirconia can be used to modify a surface layer of the material arrangements, such as the denture base, to overcome certain known shortcomings of the modified materials, e.g., typical acrylic resins containing nanosilver and nanozirconia.

19 Claims, 20 Drawing Sheets

(56) References Cited

U.S. PATENT DOCUMENTS

2018/0325782 A1    11/2018   Gad et al.
2018/0327614 A1*   11/2018   Gad .................... C08L 33/12

OTHER PUBLICATIONS

Major Repair SDS, Major Perodotti Dentari S.P.A., Jun. 25, 2019 (Year: 2019).*

Souza Neto, et al. ; Effect of synthetic colloidal nanoparticles in acrylic resin of dental use ; European Polymer Journal 112 ; pp. 531-538 ; 2019 ; 8 Pages.

Zhang, et al. ; The antifungal effects and mechanical properties of silver bromide/cationic polymer nanocomposite-modified Poly-methyl methacrylate-based dental resin Scientific Reports 7: 1547 ; May 8, 2017 ; 13 Pages.

Acosta-Torres, et al. ; Cytocompatible antifungal acrylic resin containing silver nanoparticles for dentures ; Dovepress International Journal of Nanomedicine ; Aug. 31, 2012 ; 11 Pages.

Arenas-Arrocena, et al. ; New Trends for the Processing of Poly(Methyl Methacrylate) Biomaterial for Dental Prosthodontics ; INTECH Acrylic Polymers in Healthcare ; Apr. 2017 ; 34 Pages.

Naji S, et al. ; Recent Advances and Future Perspectives for Reinforcement of Poly(methyl methacrylate) Denture Base Materials: A Literature Review ; Journal of Biomaterials (5)(1) ; Jan. 8, 2018 ; 13 Pages.

* cited by examiner

DOUBLE-LAYERED DENTURE COMPRISING NANOPARTICLES

BACKGROUND OF THE INVENTION

Field of the Invention

The present disclosure relates to biomedical devices, particularly to dental materials such as denture, bridge, implant, etc., materials, as well as to making and using such materials, preferably for improved prophylaxis in dental devices.

Description of the Related Art

Denture stomatitis (DS), also referred to as denture sore mouth, chronic atrophic candidiasis, *Candida*-associated denture induced stomatitis, or denture-associated erythematous stomatitis, is a common inconvenience for complete denture wearers, and potentially also for partial denture users. Denture-related stomatitis is a common condition where mild inflammation and redness of the oral mucous membrane occurs, especially beneath a denture. Generally, *Candida* species are involved, which are normally harmless components of the oral microbiota, but in certain cases can lead to oral candidiasis which is a yeast infection of the mouth. Denture stomatitis is most common in wearing a complete upper denture, i.e., a denture which replaces all the upper teeth, worn by someone with no natural teeth in their upper jaw. Denture stomatitis often results from infrequent removal and/or irregular cleaning of the denture.

Denture base materials can contribute in the occurrence of denture stomatitis (DS), as the surface topography and base material (e.g., acrylic) hydrophobicity can promote microbial attachment and biofilm formation. The main pathogen responsible of denture stomatitis (DS) is *Candida albicans*. The use of acrylic resin that is resistant to *candida* adhesion has been hypothesized to an effective way to avoid development of denture stomatitis (DS). Hygienic denture materials (containing antifungal agents) could be relevant in sustaining oral and systemic health in patients utilizing acrylic dentures.

Recently, the addition of nano-particles to polymethylmethacrylate (PMMA) has gained attention in certain applications because PMMA nano-particles have shown improved mechanical and/or physical properties as well as microbial resistance. The antimicrobial effect appears to be related to the surface energy of nano-particles and chemical reactivity. Incorporating nano-materials into denture base acrylic could be advantageous if such nano-materials provide an antibacterial effect, which may be related to the magnitude of the active surface area compared to their size. As a result, high surface area nano-materials might provide higher activity in small concentrations. Nano-sized silver (Ag) particles added to PMMA have shown improved resistance to bacterial and fungal colonization, but the mechanical properties of Ag-PMMA nano-composites were negatively affected.

Silver nano-particles (Ag-NPs) can exhibit antimicrobial activity and have gained attention in the development of a number of antibacterial materials. Silver nano-particles (Ag-NPs) are well-tolerated by living tissues and have a low degree of cytotoxicity or genotoxicity in comparison to antibiotics. Silver nano-particles (Ag-NPs) generally have a low tendency to induce microbial resistance, but are not widely used in dental materials. Recent studies investigating silver-containing nano-materials have concluded that the bacterial toxicity, or bactericidal activity, of silver nano-material fillers is mainly due to damage of cell membrane and disruption of ion homeostasis, with unclear effects on human health.

Previous studies have shown that the addition of silver nano-particles (Ag-NPs) can increase thermal conductivity, e.g., with 5 to 30 wt. % of silver nano-particles (Ag-NPs), when added to an acrylic resin thereby increasing the coefficient of thermal conductivity 1.67-fold to 4.53-fold. Palatal acrylic resins containing silver nano-particles (Ag-NPs) can have enhanced thermal conductivity and improved patient taste sensation, in addition to improved impact strength.

A disadvantage of silver nano-particles (Ag-NPs) is their effect on acrylic resin color, limiting the use of silver nano-particles (Ag-NPs) in aesthetic applications. In addition, silver nano-particles (Ag-NPs) can have a negative effect on the tensile strength of acrylic resin. A study using 5 wt. % silver nano-particles (Ag-NPs) in order to minimize the probable adverse effects on the mechanical and chemical properties of acrylic resins found that an unfavorable brownish discoloration of the dentures was a significant issue. Another factor for choosing lower percentages of silver nano-particles (Ag-NPs) could also be to lower the cost of dentures containing silver nano-particles (Ag-NPs).

Zirconium oxide, or zirconia, nano-particles ($ZrO_2$-NPs) have also gained popularity due to their potential antimicrobial properties. The characteristics and surface properties of zirconia nano-particles ($ZrO_2$-NPs) may make them a suitable additive for polymer reinforcement if incorporated in the correct ratio. Studies have indicated antifungal effects of zirconia nano-particles ($ZrO_2$-NPs) on *C. albicans* and *Aspergillus niger*. Zirconia nano-particles ($ZrO_2$-NPs have been reported to primarily affect *Escherichia coli*, *Staphylococcus aureus*, and *A. niger*).

The antifungal properties of zirconia nano-particles ($ZrO_2$-NPs) may also be a consequence of high surface area. The antifungal activity may occur through the deformation of fungal hyphae causing a disruption of cell function. The antifungal effect of zirconia nano-particles ($ZrO_2$-NPs) has been investigated, reaching a conclusion that $ZrO_2$-NP-modified acrylic resin exhibited antifungal effects against *C. albicans*, and may be useful to prevent denture stomatitis (DS). It has been speculated that adding zirconia nano-particles to auto-polymerized resin could reduce *C. albicans* adhesion on the surfaces of PMMA prostheses. However, the translucency of denture bases modified by zirconia nano-particles ($ZrO_2$-NPs) is adversely affected. A determination of the proper concentration of $ZrO_2$-NP-reinforcement, balancing between mechanical and optical properties has been speculated to be possible.

The identification of appropriate concentrations of different nano-fillers to acrylic resin for the purpose of realizing the desirable properties of a nano-composite has been a speculative to date. High concentrations of nano-fillers can have antifungal activities, but also result in noticeable color changes in acrylic resins whereby the color shade can change from transparent pink to greyish-pink in the presence of silver nano-particles (Ag-NPs) and whitish-pink in the presence of zirconia nano-particles ($ZrO_2$-NPs). Such color changes make the final nano-composite denture base aesthetically unacceptable. Likewise, although nano-modified acrylics can show positive antimicrobial effects, mechanical and physical properties are generally adversely affected.

No antimicrobial effect related to nano-particles on an intaglio surface of a denture base corresponding with the effects of internal particles within the resin matrix has been reported. However, other research in the field warrants mention.

US 2018/0325782 A1 by Gad et al. (Gad) discloses a method of preventing or treating an oral disease by reducing adhesion of microorganisms, e.g., *Candida albicans*, to dental appliances fabricated and/or repaired by an autopolymerizing acrylic reinforcement resin comprising zirconium dioxide nanoparticles. Gad's method involves (i) dispersing a nanocomposite powder in a monomer liquid comprising MMA to form a reinforcement resin, (ii) applying the reinforcement resin to a repair gap of an acrylic dental appliance, and (iii) autopolymerizing the reinforcement resin, thereby forming a repaired dental appliance. Gad's device may have a surface layer having zirconia incorporated in PMMA resin. Gad merely investigates the effect of nanozirconia addition to a repair resin on *Candida* adhesion, disclosing neither silver nanoparticles in the reinforcement resin, nor two-layer structures.

U.S. Pat. No. 10,076,471 to Nawasrah et al. (Nawasrah) discloses a denture containing a henna powder or extract, each of which comes from pulverized henna leaves and may include any of lawsone, tannic acid, and 2-methoxy-1,4-napthoquinone and a denture fabrication material. Nawasrah's denture containing a first antimicrobial ingredient having henna powder or a henna extract, lawsone, tannic acid, and/or 2-methoxy-1,4-napthoquinone, and a second antimicrobial ingredient, and optionally, a biocompatible gel and an odor neutralizer. Nawasrah's second antimicrobial ingredient may include a silver nanoparticle, a titanium dioxide particle, a silicon compound, or an essential oil. Nawasrah requires a henna ingredient and fails to disclose zirconia nano-particles, as well as a two-layer manufacturing technique.

U.S. Pat. No. 9,675,529 to Abuelyaman et al. (Abuelyaman) discloses high refractive index monomers, and dental resins containing these. Abuelyaman's monomers include methacrylates, and Abuelyaman's compositions may include inorganic oxides, e.g. zirconia, silica, BaO, CaO, MgO, or $ZnO_2$, various glasses, etc. Abuelyaman does not describe using silver nanoparticles in the dental composition, nor two-layered denture bases from simultaneous curing.

*Eur. Polym. J.* 2019, 112, 531-538 by Neto et al. (Neto) discloses combining silver nanoparticles (Ag-NPs) with poly(methyl methacrylate) (PMMA) to reduce denture stomatitis caused by *Candida glabrata*. Neto reports the effect of different amounts of Ag-NPs in thermally polymerized PMMA, to test Ag-NPs' known antimicrobial activity. Neto reports that PMMA flexural strength decreased with higher Ag-NPs concentration, and that 0.05 wt. % Ag-NPs has greater inhibiting of biofilm formation on the PMMA surface. Neto reports that the antimicrobial property was not linearly dependent of nanoparticles concentration and was influenced by nanoparticles dispersion and distribution in the polymer matrix. Neto does not use zirconia, nor does Neto simultaneously prepare a two-layer arrangement from an autopolymerization system containing both MMA and PMMA. Neto's Ag-NPs are incorporated across the entire extent of the denture base, in the conventional manner.

*Sci. Reports* 2017, 7, 1547 by Zhang et al. (Zhang) discloses PMMA-based dental resins including a silver bromide/cationic polymer nano-composite (AgBr/NPVP), added at 0.1, 0.2, and 0.3 wt. %, for antifungal properties in preventing denture stomatitis. Zhang's composite had decreased fungal cell attachment and a relative growth rate of human dental pulp cells of higher than 75% without significantly altering the flexural strength and flexural modulus. Zhang does not disclose zirconia, nor elemental silver, nor does Zhang disclose a simultaneous preparation of two-layered arrangements with segregated doping in one layer.

*Int. J. Nanomed.* 2012, 7, 4777-4786 by Acosta-Torres et al. (Acosta) discloses PMMA and PMMA-silver nanoparticle discs to assess the antifungal effect. Acosta uses titania and ferric oxide as pigments in the PMMA, but does not mention zirconia. Acosta uses PMMA to MMA in a volume ratio of 3:1, adding silver particles along with the MMA monomer at 1 µg/mL, i.e., 0.106 wt. % AnNPs in the MMA and roughly 0.0265 wt. % in the base composition. Acosta's silver nanoparticles have an average size of 10 to 20 nm, but Acosta is silent on a double-layered, doping-segregated denture base design.

The chapter entitled "New Trends for the Processing of Poly(Methyl Methacrylate) Biomaterial for Dental Prosthodontics," in Acrylic Polymers in Healthcare, Ed. Boreddy Reddy, IntechOpen: London, 2017, DOI: 10.5772/66610, by Arenas-Arrocena et al. (Arenas) discloses approaches to prevent denture stomatitis in dental implants and/or dental prosthetics made of PMMA. Arenas describes surface modified PMMA materials coated with silver nanoparticles (or copper, zinc oxide, titanium oxide, or other metal oxides) by spin coating. Arenas's coating comprises pure silver nanoparticles, rather than a second PMMA layer having a certain percentage of silver nanoparticles dispersed within the resin matrix.

*J. Dental Biomater.* 2018, 5(1), 490-502 by Abdulrazzaq Naji et al. (Naji) discloses PMMA complete and partial dentures and prosthetics containing high surface area to volume nanoparticles comprising silver, titania, zirconia, alumina, and/or ceramic. Naji evaluates the reinforcement potential of nanofiber and nanotubes in PMMA denture base resins, reporting broad-spectrum antimicrobial activity for silver nanoparticles, as well as generically improved mechanical properties upon adding Ag, $TiO_2$, $ZrO_2$, $Al_2O_3$, and ceramic nanoparticles. However, Naji ignores opacity and fails to describe a double-layered dental restoration design having segregated layer-doping.

In light of the above, a need remains for improved prosthetic materials, particularly for dental applications, such as dentures, wherein the translucency and mechanical strength are less compromised by the addition of antimicrobial components, as well methods of making such materials, particularly in segregated structural arrangements.

SUMMARY OF THE INVENTION

Aspects of the invention provide dental restoration base materials comprising: a first layer comprising at least 90 wt. %, relative to total first layer weight, of a cured first composition comprising, prior to curing, a first (meth)acrylic polymer and a first (meth)acrylic monomer; and a surface layer comprising at least 90 wt. %, relative to total surface layer weight, of a cured second composition comprising, prior to curing, a second (meth)acrylic polymer, a second (meth)acrylic monomer, and 0.1 to 5 wt. % of antimicrobial nanoparticles, relative to a total surface layer weight, wherein no gradient in antimicrobial nanoparticle content and no continuous bulk containing the antimicrobial nanoparticles is present between the first and surface layers, and wherein the first layer comprises no more than 10% as much of the antimicrobial particles as the surface layer. Such materials may be modified by any permutation of the features described herein, particularly the following.

Inventive materials may comprise 0.25 to 2 wt. % of the antimicrobial nanoparticles, and/or the antimicrobial nanoparticles may comprise silver nanoparticles optionally having an average particle size of 5 to 40 nm.

Inventive materials may comprise 0.25 to 2 wt. % of the antimicrobial nanoparticles, and/or the antimicrobial nanoparticles comprise zirconium dioxide nanoparticles optionally having an average particle size of 20 to 60 nm.

The antimicrobial nanoparticles may comprise silver nanoparticles and zirconium dioxide nanoparticles. The antimicrobial nanoparticles may comprise no more than 0.1 wt. % organic compounds, relative to the total material weight.

The surface layer may directly contact the first layer on at least portions of the first layer. Inventive materials may be arranged such that, in operation, the surface layer is configured to contact oral fluids and to shield any layers below the surface layer, including the first layer, from the oral fluids. The first layer may be at least partially in contact with oral fluids on the cameo side, but not the oral tissues at least on the cameo side, and/or at least partially shielded from oral fluid(s) on the intaglio side, e.g., while being at least partially to entirely shielded from contact with the oral tissue(s), particularly gums. The surface layer may have a thickness no more than 20% that of a total material thickness. The surface layer may have a thickness of 100 to 3,000 μm, 115 to 2,000 μm, 125 to 1,000 μm, or 150 to 750 μm.

The first (meth) acrylic polymer and the second (meth) acrylic polymer may each comprise at least 90 wt. % poly(methyl methacrylate). The first (meth)acrylic monomer and the second (meth)acrylic monomer may each comprise at least 90 wt. % methyl methacrylate. The first (meth) acrylic polymer and the second (meth)acrylic polymer may be the same (material), and/or the first (meth)acrylic monomer and the second (meth)acrylic monomer may be the same (material), and/or the first and the second (meth)acrylic monomer may be suitable to form the same polymer as the first and the second (meth)acrylic polymer.

Inventive materials may be suitable to reduce *Candida* adhesion to a dental or other prosthesis or object exposed to microbes, including fungi, by at least 10%, relative to materials comprising the first layer alone.

Inventive materials may have a flexural strength in a range of from 60 to 100 MPa. Inventive materials may have a translucency parameter in a range of from 2 to 15. The surface layer and/or the inventive materials may have a surface roughness in a range of from 0.1 to 0.4 μm.

Aspects of the invention provide dentures comprising any permutation of the inventive dental restoration base material described herein.

Aspects of the invention provide methods of preventing or reducing adhesion of a microorganism to a dental restoration, the method comprising inserting into an oral cavity of a subject in need thereof the dental restoration comprising any permutation of the inventive dental restoration base material described herein; and maintaining the dental restoration in the oral cavity for at least 3 hours. The microorganism may be a *Candida* species of fungus.

Aspects of the invention provide methods of making a dental restoration base material, which methods may comprise: prepolymerizing a first composition comprising a first (meth)acrylic monomer and a first (meth)acrylic polymer, to obtain a first viscous composition; conforming the first viscous composition into a dental mold; prepolymerizing a second composition comprising a second (meth)acrylic monomer, 0.1 to 5 wt. %, relative to a total second composition weight, of antimicrobial nanoparticles, and a second (meth)acrylic polymer, to obtain a second viscous composition; conforming the second viscous composition into the dental mold over the first viscous composition; polymerizing the first and second viscous compositions in the dental mold, thereby forming a restoration base material.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1A:
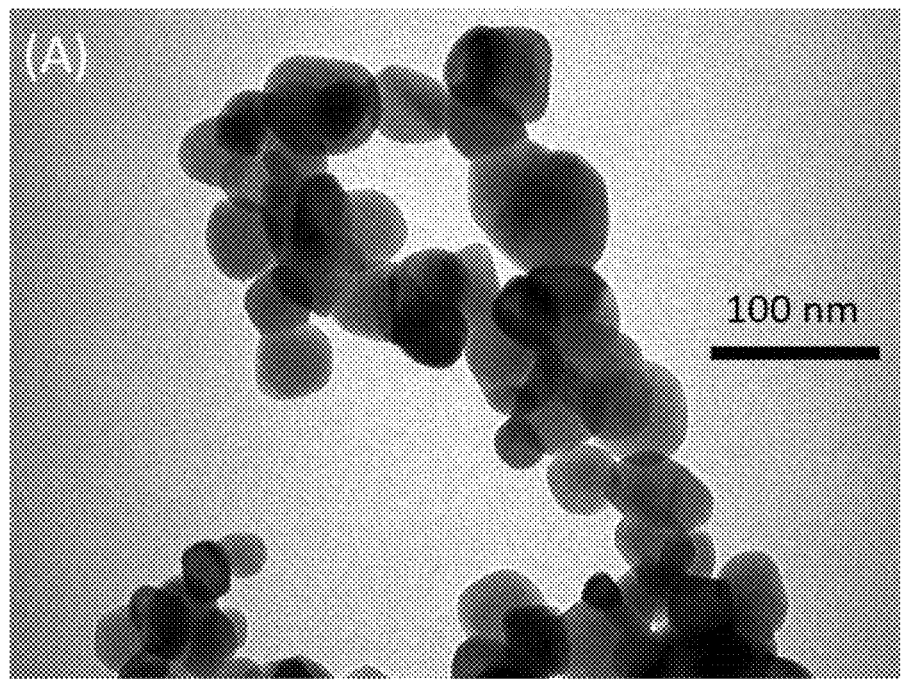
FIG. 1A shows a transmission electron microscopy (TEM) image of zirconia nano-particles ($ZrO_2$-NPs) of the type used in the Examples.

Aspects of the invention provide dental restoration base materials (i.e., suitable for dentures, bridges, retainer forms, and other prostheses) comprising: a first layer comprising at least 90, 92.5, 95, 97.5, 98, 99, 99.1, 99.5, or 99.9 wt. %, relative to total first layer weight, of a cured first composition comprising, prior to curing, a first (meth)acrylic polymer and a first (meth)acrylic monomer; and a surface layer comprising at least 90, 92.5, 95, 97.5, 98, 99, 99.1, 99.5, or 99.9 wt. %, relative to total surface layer weight, of a cured second composition comprising, prior to curing, a second (meth)acrylic polymer, a second (meth)acrylic monomer, and 0.1 to 5 wt. %, e.g., at least 0.1, 0.15, 0.2, 0.25, 0.3, 0.33, 0.35, 0.4, 0.45, 0.5, 0.55, 0.6, 0.65, 0.67, 0.7, 0.75, 0.8, 0.85, 0.9, 0.95, or 1 wt. % and/or up to 5, 4.75, 4.5, 4.25, 4, 3.75, 3.5, 3.25, 3, 2.75, 2.5, 2.33, 2.25, 2.125, 2, 1.875, 1.75, 1.67, 1.6, 1.5, 1.45, 1.4, 1.33, 1.3, 1.25, 1.125, or 1 wt. % of antimicrobial nanoparticles, relative to a total surface layer weight. In the first layer, the polymer and monomer may make out, e.g., 90, 91, 92, 92.5, 93, 94, 95, 96, 97, 97.5, 98, 99, 99.1, 99.5, 99.9, or 99.99 wt. % of the first composition, whereas there should generally be an allowance in the second composition for the antimicrobial nanoparticles, e.g., up to 5, 4, 3, 2.5, 2, 1, 0.5, 0.1 wt. % and/or at least 0.1, 0.25, 0.33, 0.5, 0.75, 0.85, 1, 1.1, 1.15, 1.25, 1.33, 1.4, or 1.5 wt. %, with a remainder or at least 90, 91, 92, 92.5, 93, 94, 95, 96, 97, 97.5, 98, 99, 99.1, 99.5, 99.9, or 99.99 wt. % of the remainder generally being the polymer/monomer content.

"Cured," as used herein, may mean a partially cured form of the first and/or second composition, sufficiently non-fluid for commercial delivery, up to a completely cured finished product. Generally, there will be no gradient in antimicrobial nanoparticle content between the first layer and the surface layer, wherein "no gradient" means that the transition between the first and surface layer is discrete, rather than a continuum of particle content within a single layer, even though the first and surface layers may be a part of a single, integral solid, even directly bordering each other as an apparently contiguous mass. For example, an interface between the surface and the first layer may manifest a sharp change in filler content, such as 90, 91, 92, 92.5, 93, 94, 95, 96, 97, 97.5, 98, 99, 99.1, 99.5, 99.9, 99.99, 99.999, 99.9999, or even 100% drop-off in filler content. For example, the filler content may go from 1.5 wt. % in the first layer to 0.1, 0.01, 0.001, 0.0001, 0.00001, or even 0 wt. % in the first layer at the surface of the first layer oriented towards the surface layer, or within 500, 400, 350, 300, 250, 200, 150, 100, 75, 50, 25, 20, 15, 10, 7.5, 5, 2.5, 1, 0.5, 0.1, or 0.01 m of the first layer surface.

In inventive base materials, there is likewise generally no continuous bulk containing the antimicrobial nanoparticles present between the first and surface layers, in that although the matrix may be a continuous bulk, there is generally an interruption of antimicrobial nanoparticles content between the first and the surface layer. The first and surfaces layers are generally adhered to each other via polymerization of their own bulk, rather than by an extraneous adhesive or mechanical fixture. For example, the first layer will be generally completely free of the antimicrobial nanoparticles, or the first layer may comprise no more than 10, 7.5, 5, 4, 3, 2.5, 2, 1, 0.5, 0.1, 0.01, 0.001, 0.0001, or 0.00001% as much of the antimicrobial particles as the surface layer.

Inventive materials may comprise 0.25 to 2 wt. %, or 0.33 to 1.67 wt. %, or 0.5 to 1.5 wt. %, or 0.67 to 1.25 wt. %, or 0.75 to 1 wt. % (or any combination of these endpoints or those above) of the antimicrobial nanoparticles, and/or the antimicrobial nanoparticles may comprise silver nanoparticles, e.g., at least 75, 80, 85, 90, 91, 92, 92.5, 93, 94, 95, 96, 97, 97.5, 98, 99, 99.1, 99.5, or 99.9 wt. % of a total weight of the antimicrobial nanoparticles, optionally having an average particle size (or longest dimension) of 5 to 40 nm, e.g., at least 5, 6, 7, 8, 9, 10, 12.5, or 15 nm and/or up to 40, 35, 30, 27.5, 25, 22.5, or 20 nm.

Inventive materials may comprise 0.25 to 2 wt. %, or 0.33 to 1.67 wt. %, or 0.5 to 1.5 wt. %, or 0.67 to 1.25 wt. %, or 0.75 to 1 wt. % (or any combination of these endpoints or those above) of the antimicrobial nanoparticles, and/or the antimicrobial nanoparticles comprise zirconium dioxide (i.e., zirconia) nanoparticles, e.g., at least 75, 80, 85, 90, 91, 92, 92.5, 93, 94, 95, 96, 97, 97.5, 98, 99, 99.1, 99.5, or 99.9 wt. % of a total weight of the antimicrobial nanoparticles, optionally having an average particle size (or longest dimension) of 20 to 60 nm, e.g., at least 20, 22.5, 25, 27.5, 30, 32.5, or 35 nm and/or up to 60, 57.5, 55, 52.5, 50, 47.5, 45, 42.5, or 40 nm. The sphericity of the silver and/or zirconia nanoparticles is generally at least 0.875, 0.9, 0.91, 0.92, 0.925, 0.93, 0.935, 0.94, 0.945, 0.95, 0.955, 0.96, 0.965, 0.97, 0.975, 0.98, 0.985, or 0.99.

The antimicrobial nanoparticles may comprise silver nanoparticles and zirconium dioxide nanoparticles, e.g., as at least 25, 35, 40, 45, 47.5, 48, 49, 49.5, 49.9, 50, 60, 70, 75, 80, 85, 90, 95, 97.5, 98, 98.5, 99, 99.5, or 99.9 wt. % of the total antimicrobial (nanoparticle) weight, either individually or in combination, as is mathematically feasible. While "nanoparticles" is generally used herein to reference the morphology of the antimicrobial materials, and spheroid shapes may be preferred in some applications, fibers, prisms, rods, tubes, and the like may also be acceptable morphologies. The antimicrobial nanoparticles may comprise no more than 5, 4, 3, 2.5, 2, 1, 0.5, 0.1, 0.01, 0.001, 0.0001, or 0.00001 wt. % organic compounds, relative to the total base material weight or antimicrobial weight.

The surface layer may directly contact the first layer on at least portions of the first layer or, e.g., on at least 50, 60, 70, 75, 80, 85, 90, 95, or 100% of the outer (interaglio-side facing) surface area of the first layer. Certain applications may also allow for 1, 2, 3, 4, or more intervening layers, which may comprise the same or substantially similar polymeric matrix, as desired. Inventive materials may be arranged such that, in operation, the surface layer is configured to contact oral fluids, i.e., within the mouth, either on the gums, or by the tongue, or digestive fluids temporarily or generally in the oral cavity. The surface layer may shield any layers below the surface layer, including the first layer, from such oral and/or digestive fluids. The surface layer may have a thickness of no more than 20, 17.5, 15, 10, 7.5, 5, 4, 3, 2, 1, or 0.5%, and/or at least 0.1, 0.25, 0.5, 0.75, 1, 2.5, 3.33, 5, 7.5, or 10%, that of a total base material (or dental prosthesis thickness (e.g., from the center of mass, when based upon irregular shapes). The surface layer may have a thickness of 100 to 3,000 μm, e.g., at least 100, 150, 200, 250, 300, 350, 400, 450, 500, 550, 600, 650, 700, or 750 μm and/or up to 3000, 2750, 2500, 2250, 2000, 1750, 1650, 1500, 1450, 1400, 1350, 1300, 1250, 1200, 1150, 1100, 1050, or 1000 μm.

The first (meth)acrylic polymer and the second (meth)acrylic polymer may each comprise at least 90, 91, 92, 92.5, 93, 94, 95, 96, 97, 97.5, 98, 99, 99.1, 99.5, or 99.9 wt. % poly(methyl methacrylate). The first (meth)acrylic monomer and the second (meth)acrylic monomer may each comprise at least 90, 91, 92, 92.5, 93, 94, 95, 96, 97, 97.5, 98, 99, 99.1, 99.5, or 99.9 wt. % methyl methacrylate. The first (meth)acrylic polymer and the second (meth)acrylic polymer may be the same (material), and/or the first (meth)acrylic monomer and the second (meth)acrylic monomer may be the same (material), and/or the first and the second (meth)acrylic monomer may be suitable to form the same polymer as the first and the second (meth)acrylic polymer. For example, the cured material may be a PMMA matrix, and/or may contain any of the polymerized (after curing) monomers described below.

Inventive materials may be suitable to reduce *Candida* adhesion to a dental or other prosthesis or object exposed to microbes, including fungi, by at least 10, 15, 20, 25, 33, 40, 50, 60, 70, 75, 80, 85, 90, or 95%, relative to materials comprising the first layer alone.

Inventive materials may have a flexural strength in a range of from 60 to 100 MPa. Inventive materials may have a translucency parameter in a range of from 2 to 15. The surface layer and/or the inventive materials may have a surface roughness in a range of from 0.1 to 0.4 μm. Inventive dental restoratives may have a flexural strength in a range of from 79 to 90 MPa, e.g., at least 65, 67.5, 70, 72.5, 75, 77.5, 79, 80, 81, 82, 83, 84, or 85 MPa and/or up to 100, 97.5, 95, 92.5, 90, 89, 88, 87.5, 87, 86, 85.5, or 85 MPa, and/or a translucency parameter in a range of from 3 to 13, e.g., at least 2, 2.5, 3, 3.5, 4, 4.5, 5, 5.5, 6, 6.5, 7, 7.5, or 8 and/or up to 15, 14, 13, 12.5, 12, 11.5, 11, 10.5, 10, 9.5, 8.5, or 8. The surface layer may have a surface roughness (Ra) in a range of from 0.12 to 0.35 m, e.g., at least 0.1, 0.11, 0.12, 0.13, 0.14, 0.15, 0.175, or 0.2 μm and/or up to 0.4, 0.375, 0.35, 0.325, 0.3, 0.275, 0.25, 0.225, 0.2, or 0.175 μm.

Aspects of the invention provide dentures, partial dentures, palatal obturators, orthodontic appliances, retainers, dental implants, crowns, bridges, and/or other oral maxillofacial prostheses, typically as a base material, comprising any permutation of the inventive dental restoration base material described herein.

Aspects of the invention provide methods of preventing or reducing adhesion of a microorganism to a dental restoration, the method comprising inserting into an oral cavity of a subject in need thereof the dental restoration (e.g., dentures, partial dentures, palatal obturators, orthodontic appliances, retainers, dental implants, crowns, bridges, and/or other oral maxillofacial prostheses) comprising any permutation of the inventive dental restoration base material described herein; and maintaining the dental restoration in the oral cavity for at least 3, 5, 8, 12, 16, 20, 24, or more hours. The microorganism may be a *Candida* species of fungus. Such methods may show one or more of antifungal, antibacterial/bactericidal, anti-protozoal, etc., effects.

Aspects of the invention provide methods of making a dental restoration base material, which methods may comprise: prepolymerizing a first composition comprising a first (meth)acrylic monomer and a first (meth)acrylic polymer, to obtain a first viscous composition (e.g., increasing the viscosity, decreasing the volatility, or the like, to provide a dough-like or Bingham fluid-like phase); conforming the first viscous composition into a dental mold; prepolymerizing (e.g., increasing the viscosity, decreasing the volatility, or the like, to provide a dough-like or Bingham fluid-like phase) a second composition comprising a second (meth)acrylic monomer, 0.1 to 5 wt. % (or any amount described above or elsewhere herein), relative to a total second composition weight, of antimicrobial nanoparticles, and a second (meth)acrylic polymer, to obtain a second viscous composition; conforming the second viscous composition into the dental mold over the first viscous composition; polymerizing (e.g., by heating and/or irradiation) the first and second viscous compositions in the dental mold, thereby forming a restoration base material.

The "prepolymerizing" may occur under normal ambient conditions, with milling, and/or with applied pressure, e.g., at least 2500, 3500, 5000, 6000, 7000, 7500, or 8000 N and/or up to 10 k, 9.5 k, 9 k, 8.5 k, 8 k, 7.5 k, or 7 k N (pressures which may be used in the first "conforming" to press the first solution into the form), though generally without additional irradiation and/or heating. The monomers and polymers may be any of those described below, but may preferably contain methyl methacrylate. A weight percent of monomer relative to polymer composition (monomer plus polymer), may be in a range of, e.g., at least 25, 27.5, 30, 32.5, 35, 37.5, 40, 40.5, 41, 42, 43, 44, or 45 wt. % (w/w) and/or up to 55, 52.5, 50, 47.5, 47, 46.5, 46, 45.5, 45, 44.5, 44, 43.5, 43, 42.5, 42, or 41.5 wt. % (w/w). The application of the two compositions, i.e., "conforming" the solutions, into a form, may take place at one at the aforementioned pressure, and/or at a pressure in the range of from, e.g., at least 8, 8.5, 9, 9.5, 10, 10.5, 11, 11.5, 12, or 12.5 kN and/or up to 15, 14.75, 14.5, 14.25, 14, 13.75, 13.5, 13.25, 13, 12.75, 12.5, 12.25, or 12 kN. The first composition may be added to the mold with protective (inert and/or non-reactive) films, foils, or otherwise, such as cellophane, PE, aluminum, tin, wax, etc., to shield the first composition from the mold surfaces and/or prevent flow from a retained area, e.g., to allow/reserve space for the second composition in the mold.

The heating, if used to polymerize the first and/or second compositions, may be, e.g., at a temperature of at least 60, 65, 67.5, 70, 72.5, 75, 77.5, or 80° C. and/or up to 100, 95, 90, 85, 82.5, 80, 77.5, or 75° C. for, e.g., at least 3, 4, 5, 6, 7, or 8 hours and/or up to 12, 11, 10, 9, 8, 7, or 6 hours, then optionally at a higher temperature, e.g., 1.2, 1.25, 1.3, 1.4, 1.45, 1.5-fold the original temperature or range, for a period of at least 20, 30, 35, 40, 45, 50, 55, or 60 minutes and/or up to 120, 105, 90, 85, 80, 75, 70, 65, or 60 minutes.

Aspects of the invention comprise packing two (or more) layers, including at least a pure and a modified layer, of heat-cure acrylic resin into the mold space as a viscous, dough-like phase, then simultaneously processing the layers to form the final heterogeneous denture base including a pure acrylic resin on the cameo side of the denture and antifungal-modified acrylic resin on the intaglio side of the denture. Aspects of the invention can avoid sequential methods, or coating after the formation of a base layer.

Aspects of the invention include a thin layer of antifungal-modified resin to conventional resin during packing procedures. Aspects of the invention provide a difference, i.e., reduction, in *Candida* adhesion between the modified one-layer and double-layer complete denture bases. Aspects of the invention provide a difference in flexural strength, surface roughness, and/or translucency between the modified one-layer and two-layer complete denture bases.

Aspects of the invention comprise eliminating and/or reducing, e.g., by 15, 25, 35, 50, 60, 70, 75, 80, 85, 90, 92.5, 95, 97.5, or 99%, or more, erythematous (redness), edematous (swelling), angular cheilitis (oral corner inflammation), and/or petechial hemorrhage (pin-points of bleeding). Such effects may be achieved anywhere in the mouth, or other mucosal orifice in which an inventive device is applied, particularly beneath an upper denture and/or under a lower denture.

Aspects of the invention include dental restorations comprising (i) a base restoration which includes a cured form of a first composition containing a monomer liquid comprising methyl methacrylate and a polymer powder comprising polymethyl methacrylate, and/or (ii) a surface layer including a cured form of a second composition containing a monomer liquid comprising methyl methacrylate (MMA), and a nanocomposite powder containing a polymer powder comprising polymethyl methacrylate (PMMA), and 0.5 to 1.5 wt. % antimicrobial nanoparticles relative to a total weight of the nanocomposite powder, wherein at least a portion of a surface of the base restoration is coated by the surface layer. The surface layer—generally the filled layer—may have a thickness a range of from 100 to 3,000 μm, e.g., at least 100, 150, 250, 350, 500, 750, or 1000 μm and/or up to 3, 2.5, 2, 1.75, 1.5, 1.25, 1.1, 1, 0.9, 0.8, 0.75, 0.7, 0.65, 0.6, 0.55, or 0.5 mm, and is generally directed towards and/or contacting the oral surfaces and/or fluids.

The antimicrobial nanoparticles may include silver nanoparticles having an average particle size a range of from 10 to 40 nm, zirconium dioxide nanoparticles having an average particle size a range of from 20 to 50 nm, or both. The antimicrobial particles may be covered by a silane coating via treatment with a silane coupling reagent. The zirconia nano-particles ($ZrO_2$-NPs) and/or silver nano-particles (Ag-NPs) may have no surface treatment, or may have no more than 25, 20, 15, 10, 5, 4, 3, 2, 1, 0.5, 0.1, 0.001, or 0.0001 wt. % or no more than trace detectable amounts of surface treatment, such as silane, amine, sulfone, etc. groups. The silver may be in elemental form and/or contain no silver ($Ag^+$) ions, or, for example, contain no more than 10, 8, 7.5, 7, 6, 5, 4, 3, 2.5, 2, 1, or 0.5 wt. % silver ions, relative to total silver weight.

Aspects of the invention include methods of preventing and/or reducing adhesion of one or more microorganisms (e.g. *Candida* species) to a dental restoration. Adhesion may be reduced by, e.g., at least 10, 15, 25, 33, 40, 50, 60, 70, 75, 80, 85, 90, or 95%, relative to materials without additives.

Aspects of the invention comprise including zirconia nano-particles ($ZrO_2$-NPs) and silver nano-particles (Ag-NPs) in one- and two-layer denture bases reduced *candida* adhesion. Including zirconia nano-particles ($ZrO_2$-NPs) in one- or two-layer denture bases can increase the flexural strength, e.g., at least 2.5, 5, 7.5, 10, 12.5, 15, 17.5, 20, 25, 33%, or more and/or up to 75, 67, 60, 50, 40, 33, 25, 20, or 15%, while silver nano-particles (Ag-NPs) in one-layer denture bases may reduce the flexural strength and/or show no significant change when added in two layers. Aspects of the invention comprise avoiding modification of the surface roughness of a denture base with zirconia nano-particles ($ZrO_2$-NPs) in one-layer and/or two-layer arrangements, e.g., no more than 15, 10, 7.5, 5, 4, 3, 2, 1, 0.5, or 0.1%, optionally while modifying the surface roughness of a one-layer and/or two-layer denture base with silver nano-particles (Ag-NPs), e.g., at least 1, 2.5, 5, 7.5, 10, 12.5, 15, 17.5, 20, 25, 33%, or more and/or up to 75, 67, 60, 50, 40, 33, 25, 20, or 15%.

Aspects of the invention comprise reducing a translucency value, e.g., at least 0.5, 1, 2, 3, 4, 5, 7.5, 10, 15, 20, 25, 33, 40%, or more and/or up to 75, 67, 60, 50, 40, 33, 25, 20, or 15%, of one-layer and/or two-layer denture bases modified with zirconia nano-particles ($ZrO_2$-NPs) or silver nano-particles (Ag-NPs), and/or reducing the translucency diminution by using a two-layer modified denture base versus a one-layer modified denture base for zirconia nano-particles ($ZrO_2$-NPs) and/or silver nano-particles (Ag-NPs), e.g., up to 15, 10, 7.5, 5, 4, 3, 2, 1, 0.5, or 0.1%.

Aspects of the invention include methods for antifungal activity via nano-filler addition without detrimental effects, e.g., independently no more than 15, 10, 7.5, 5, 4, 3, 2, 1, 0.5, or 0.10, relative to unfilled arrangements, on the mechanical properties, such as impact strength, tensile strength, roughness, and/or translucency, of final nano-composite denture base material.

Useful acrylic monomers (or homopolymers, copolymers, terpolymers, etc., thereof) may include thermoplastic or thermosetting plastic substances derived from acrylate and/or methacrylate, in protonated, esterified, and/or deprotonated form (etc.). Poly(methyl methacrylate) (PMMA) is also known as acrylic or acrylic glass as well as by the trade names Plexiglas, Acrylite, Lucite or Lucitone, and Perspex, among others, typically referring to a transparent thermoplastic. Chemically polymerized, heat polymerized, and/or light polymerized compositions may be used. Useful monomers may include, for example, methyl (meth)acrylate, isopropyl (meth)acrylate, n-propyl (meth)acrylate, isopropyl (meth)acrylate, n-butyl (meth)acrylate, isobutyl (meth)acrylate, hydroxyethyl (meth)acrylate, hydroxypropyl (meth)acrylate, hydroxybutyl (meth)acrylate, propylene glycol (meth)acrylate, poly(ethylene glycol) (meth)acrylate, isobornyl (meth)acrylate, methoxyethoxyethyl (meth)acrylate, ethoxyethoxyethyl (meth)acrylate, tetrahydrofurfuryl (meth)acrylate, 4-acetoxyethyl (meth)acrylate, phenoxyethyl (meth)acrylate, ethyleneglycol di(meth)acrylate, diethyleneglycol di(meth)acrylate, trimethyleneglycol di(meth)acrylate, triethyleneglycol di(meth)acrylate, trimethyolpropane tri(meth)acrylate, tetraethyleneglycol di(meth)acrylate, 1,3-propanediol di(meth)acrylate, 1,4-butanediol di(meth)acrylate, 1,6-hexanediol di(meth)acrylate, 1,12-dodecanediol di(meth)acrylate, polyethyleneglycol di(meth)acrylate, trimethylolpropane tri(meth)acrylate, 1,2,4-butanetriol tri(meth)acrylate, pentaerythritol tetra(meth)

acrylate, bisphenol A-glycidyl (meth)acrylate, ethoxylated bisphenol A-di(meth)acrylate, urethane di(meth)acrylate, diurethane di(meth)acrylate, polyurethane di(meth)acrylate, polycarbonate di(meth)acrylate, benzyl 2-propyl (meth) acrylate, 2-carboxyethyl (meth)acrylate, tert-butyl (meth) acrylate, di(ethylene glycol) ethyl ether (meth)acrylate, 2-hydroxy-3-phenoxypropyl (meth)acrylate, 3,5,5-trimethylhexyl (meth)acrylate, 2-tetrahydropyranyl (meth)acrylate, 10-undecenyl (meth)acrylate, lauryl acrylate, isooctyl (meth)acrylate, isodecyl (meth)acrylate, allyl (meth)acrylate, cyclohexyl (meth)acrylate, 3,3'-diethoxypropyl (meth) acrylate, diethylene glycol butyl ether (meth)acrylate, di(ethylene glycol) methyl ether (meth)acrylate, ethylene glycol dicyclopentenyl ether (meth)acrylate, 2-ethylhexyl (meth)acrylate, glycidyl (meth)acrylate, hexyl (meth)acrylate, 2-N-morpholinoethyl (meth)acrylate, 1-naphthyl (meth)acrylate, phenyl (meth)acrylate, solketal (meth)acrylate, 3,3,5-trimethylcyclohexyl (meth)acrylate, vinyl (meth) acrylate, and mixtures of 2, 3, 4, 5, or more of these. The expression "(meth)acrylate" is meant to cover acrylate or methacrylate, though methacrylates may be preferred in certain applications. All monomers and initiators described in US 2018/0325782 A1, incorporated by reference herein in its entirety, may be useful in the scope of the present invention, unless otherwise indicated. Useful (meth)acrylate esters may comprise C1 to C20 alkyl groups (straight, branched, cyclic, interrupted by O, S, or N, etc.), e.g., at least C1, C2, or C3 and/or up to C20, C18, C16, C14, C12, C10, C8, C7, C6, or C5, such as methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, norbornyl, etc. Useful monomers typically have a refractive index under 1.5, e.g., no more than 1.45, 1.4, 1.35, 1.3, 1.25, 1.2, or 1.15, and/or avoiding aryl and/or halogenated esters, though this is not a necessary feature.

Useful acrylic layers may use less than 5, 4.75, 4.5, 4.25, 3.75, 3.5, 3.25, 3, 2.75, 2.5, 2.25, 2, 1.75, 1.5, 1.25 wt. % zirconia and/or silver nanoparticles in an outermost layer, or any other layer, preferably containing no more than two layers in certain applications. Two-layer structures may exclude fillers, or zirconia nano-particles, or silver nano-particles from a first acrylic layer, and include one, both, and/or further fillers in a second layer, i.e., avoiding gradient layer structures. Useful fillers may be spherical or spheroid in form, e.g., having average sphericities of at least 0.825, 0.85, 0.88, 0.89, 0.9, 0.91, 0.92, 0.93, 0.94, 0.945, 0.95, 0.955, 0.96, 0.965, 0.97, 0.975, or 0.98.

Inventive arrangements may exclude henna powder and/or extract, including lawsone, tannic acid, and/or 2-methoxy-1,4-napthoquinone, or may include no more than 5, 4, 3, 2.5, 2, 1, 0.5, 0.1, 0.01, 0.001, 0.0001, or 0.00001 wt. %, relative to total additive weight or total denture base weight, of such henna powders and/or extracts, individually or in combination. Inventive arrangements may exclude aldehydes, e.g., 2-ethoxy benzylaldehyde, 2-isopropyl-5-methyl-2-hexenal, 5-methyl furfural, 5-methyl-thiophene-carboxaldehyde, adoxal, p-anisaldehyde, benzylaldehyde, bourgeonal, cinnamic aldehyde, cymal, decyl aldehyde, floral super, florhydral, helional, lauric aldehyde, ligustral, lyral, melonal, o-anisaldehyde, pino acetaldehyde, bucinal, thiophene carboxaldehyde, trans-4-decenal, trans trans 2,4-nonadienal, and/or undecyl aldehydes, or may include no more than 5, 4, 3, 2.5, 2, 1, 0.5, 0.1, 0.01, 0.001, 0.0001, or 0.00001 wt. %, relative to total additive weight or total denture base weight, of such aldehydes, individually or in combination. Inventive arrangements may exclude quinones, e.g., lawsone, 3-alkyl-2-hydroxy-1,4-napthoquinone, 2-amino-1,4-napthoquinone, 2-methoxy-1,4-napthoquinone, and/or 3-aminophenyl-2-hydroxy-1,4-napthoquinone, or may include no more than 5, 4, 3, 2.5, 2, 1, 0.5, 0.1, 0.01, 0.001, 0.0001, or 0.00001 wt. %, relative to total additive weight or total denture base weight, of such quinones, individually or in combination.

EXAMPLES

Preparation of Sample Molds

According to ADA specification No. 12 and ISO/DIS 1567:1998 standards (each of which is incorporated by reference herein in its entirety) for denture base resins, exemplary samples were fabricated using split press negative metal molds in dimensions of 65×10×2.5 mm for flexural strength testing and 15×2 mm discs for *Candida albicans* adhesion, translucency, and surface roughness. The molds were filled with CAVEX set up wax from Cavex (Holland), then wax samples were applied to Fujirock EP dental stone from GC using a 61B Two Flask Compress metal flask/form from Handler Manufacturing (Westfield, N.J.), i.e., a metal container suitable to invest wax specimens to create one or more mold spaces within the flask. After the setting of the stone, the wax was removed, then an Isolmajor separating medium from Major Prodotti Dentari SPA (Moncalieri, Italy) was applied. The flasks/forms were left to reach room temperature before packing the denture base materials, as described below.

Nanoparticles Used

Figure 1B:
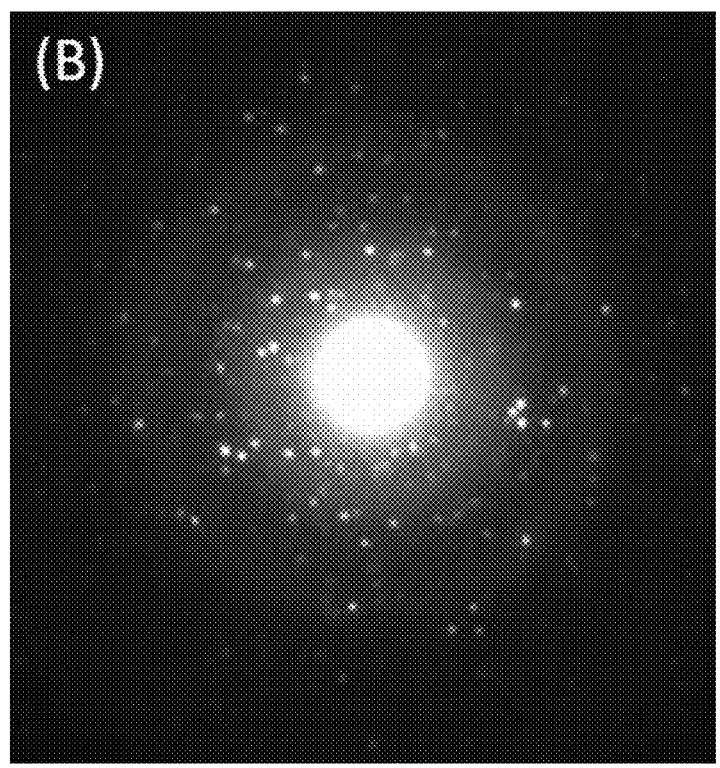
FIG. 1B shows a selected area (electron) diffraction (SAD or SAED) TEM image of zirconia nano-particles ($ZrO_2$-NPs) of the type used in the Examples.
Figure 1C:
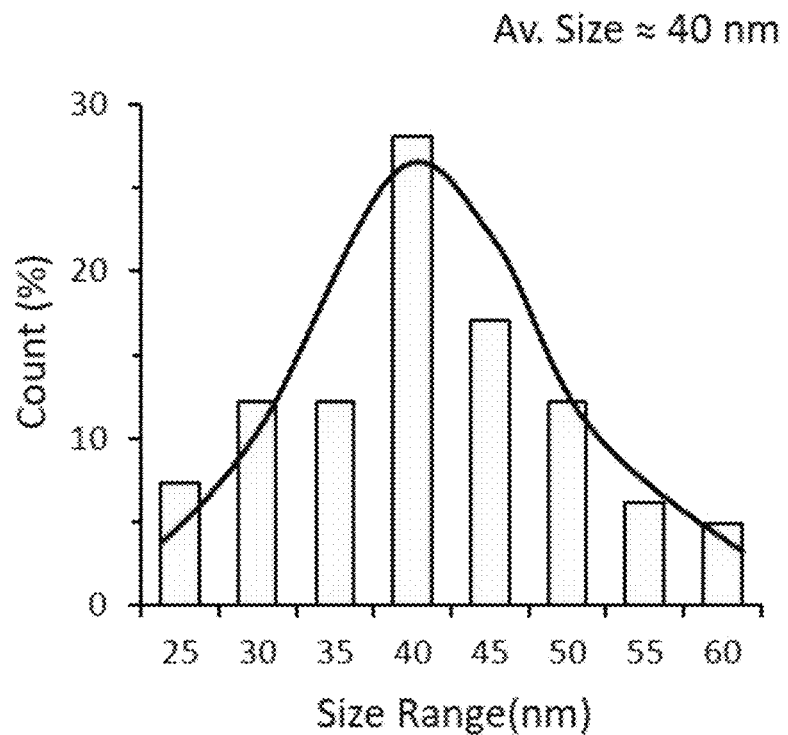
FIG. 1C shows a plot and chart of the particle size distribution histogram of the zirconia nano-particles ($ZrO_2$-NPs) of the type used in the Examples.
Figure 1D:
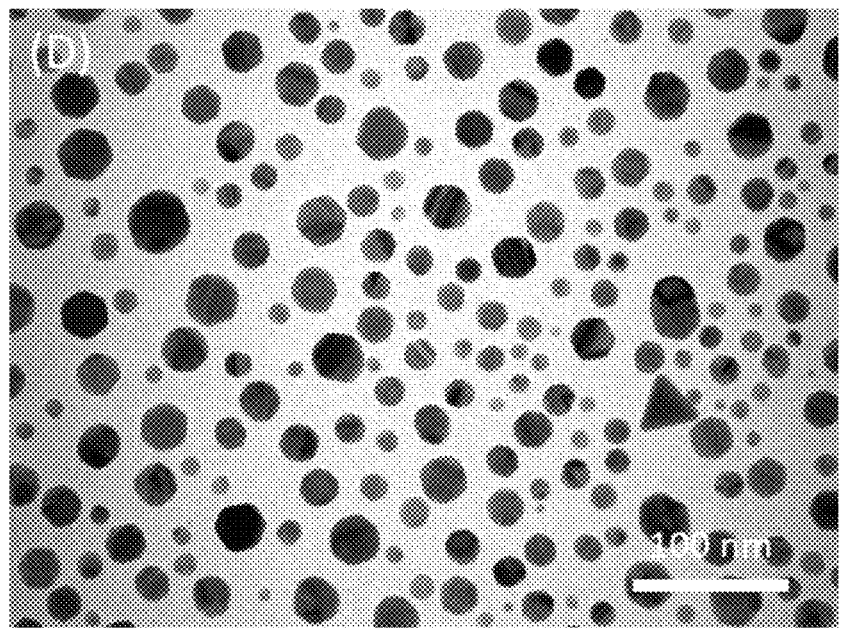
FIG. 1D shows a transmission electron microscopy (TEM) image of silver nano-particles (Ag-NPs) of the type used in the Examples.
Figure 1E:
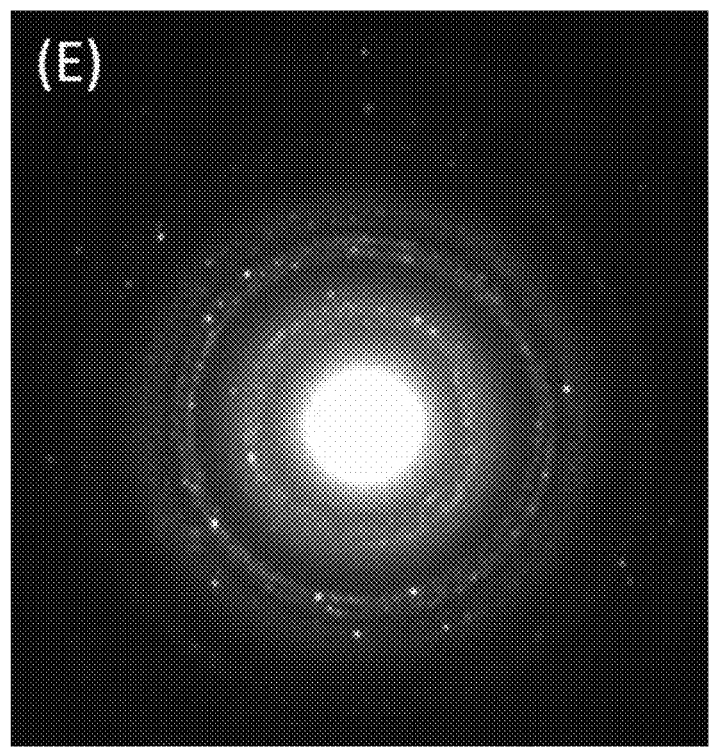
FIG. 1E shows a selected area (electron) diffraction (SAD or SAED) TEM image of silver nano-particles (Ag-NPs) of the type used in the Examples.
Figure 1F:
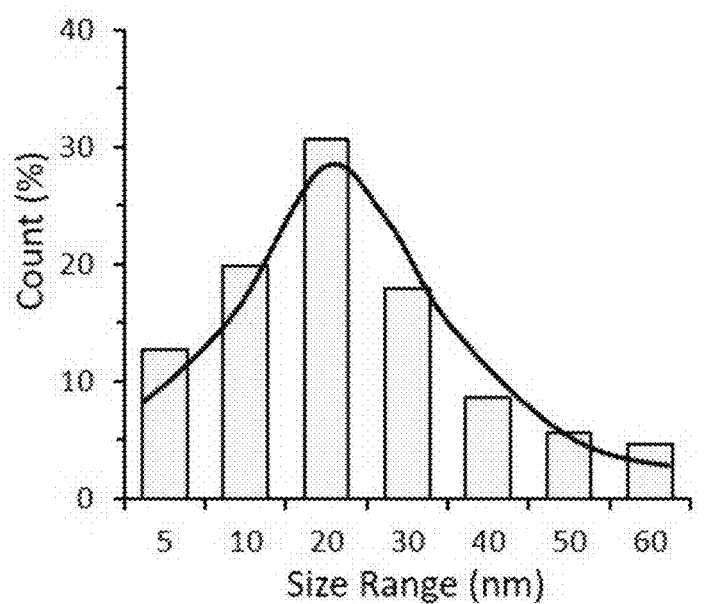
FIG. 1F shows a plot and chart of the particle size distribution histogram of silver nano-particles (Ag-NPs) of the type used in the Examples.

Transmission electron microscopy (TEM) was carried out to analyze the size, shape, and structure of zirconia nano-particles ($ZrO_2$-NPs) or silver nano-particles (Ag-NPs). The nano-fillers were dispersed in ethanol, sonicated and deposited onto TEM grids for TEM examination. The zirconia nano-particles ($ZrO_2$-NPs) of purity 99% from Shanghai Richem International Co., Ltd. (China) had an average longest dimension of 40 nm, as seen in FIG. 1A to 1C. The silver nano-particles (Ag-NPs) from Shanghai Richem International Co., Ltd. (China) used had an average granule size of 20 nm, as shown in FIG. 1D to 1F. Both nano-fillers showed crystalline structure as confirmed by electron diffraction.

Heat-polymerized acrylic resin samples were prepared according to each test specification provided below. Zirconia nano-particles ($ZrO_2$-NPs) and silver nano-particles (Ag-NPs) were added in 0.5, 1.0, and 1.5 wt. %, relative to a weight of acrylic resin powder (herein, for example, "0.5 wt. %" means that 0.5 weight parts of nano-particles were added to 99.5 wt parts of resin). Samples were divided into two groups, Group I and Group II, according to acrylic packing method.

Group I involves a one layer/one step arrangement, and Group II involves a two layers/two steps arrangement. In the one step method, acrylic was packed conventionally, i.e., by mixing and/or comminuting the PMMA, MMA, and additive, to obtain a mixture, then adding the mixture to the flask/form in a one-step method, for example, as described in Gad, M M, et al. "Comparative Effect of Different Polymerization Techniques on the Flexural and Surface Properties of Acrylic Denture Bases" *J Prosthodont.* 2019, 28(4), 458-465, which is incorporated by reference in its entirety herein. In the two step method, the packing was carried out in two layers: first, with unmodified acrylic resin, i.e., having no nanoparticles or additives, followed by a thin layer of modified acrylic resin before final closure of the flask/form. A control group made of pure acrylic resin, without additive, was prepared in one step. The flexural strength (FS), color stability, and surface roughness of the samples were measured. Microbial assays were carried out using direct culture and slide count tests. One-way ANOVA and Tukey's post hoc tests were used to identify statistical differences between groups ($\alpha=0.05$).

The addition of zirconia nano-particles ($ZrO_2$-NPs) and silver nano-particles (Ag-NPs) in one or two layers reduced *C. albicans* adhesion (P<0.001). In one and two layers, flexural strength increased with zirconia nano-particles ($ZrO_2$-NPs). Silver nano-particles (Ag-NPs) decreased flexural strength in one layer only (P<0.001). Surface roughness was not changed for one and two layers zirconia nano-particles ($ZrO_2$-NPs) and one layer 0.5 wt. % silver nano-particles (Ag-NPs) at P>0.05, while other tested silver nano-particles (Ag-NPs) concentrations increased the surface roughness, at P<0.001. Silver nano-particles (Ag-NPs) lowered translucency in one and two layers at P<0.001, while zirconia nano-particles ($ZrO_2$-NPs) decreased translucency only in one layer at P<0.001.

The addition of zirconia nano-particles ($ZrO_2$-NPs) in double layer technique decreased *Candida* adhesion, improved flexural strength, and improved translucency without effecting surface roughness, while silver nano-particles (Ag-NPs) decreased *Candida* adhesion and flexural strength, but left translucency unchanged, while increasing surface roughness.

Transmission electron microscopy (TEM) was carried out to analyze the size, shape and structure of zirconia nano-particles ($ZrO_2$-NPs) and silver nano-particles (Ag-NPs), discussed below in FIG. 1A to 1F. The nano-fillers were dispersed in ethanol, sonicated and deposited onto TEM grids for TEM examination. The nano-filler, zirconia nano-particles ($ZrO_2$-NPs) (purity 99%, Shanghai Richem International Co., Ltd. China) had an average granularity of 40 nm, shown in FIG. 1A to 1C. The silver nano-particles (Ag-NPs) from Shanghai Richem International Co., Ltd. China, used in this study had an average granule size of 20 nm, shown in FIG. 1D to 1F. Both nano-fillers showed crystalline structure as confirmed by electron diffraction.

Preparation of the Samples Containing Nano-Particles

A total of 130 samples per test were made out of heat-polymerized acrylic resin. The test groups were divided according to the number of denture base layers into two main groups: one-layer samples in Group I and two-layer samples in Group II. Each one of these groups was further divided into subgroups (n=10) according to the type ($ZrO_2$-NPs or Ag-NPs) and concentrations of nano-filler, i.e., 0.5, 1.0, and 1.5 wt. %, as seen below in Table 1.

TABLE 1

Sample grouping and description.

| Layers | Group | | Code | Description |
|---|---|---|---|---|
| (Group I) One Layer | Control, one layer, samples fabricated entirely from pure AR | | C | Unmodified acrylic resin samples |
| | One layer; samples fabricated entirely from modified AR + $ZrO_2$-NPs | | IZr 0.5% | Acrylic resin modified with 0.5% $ZrO_2$-NPs |
| | | | IZr 1.0% | Acrylic resin modified with 1.0% $ZrO_2$-NPs |
| | | | IZr 1.5% | Acrylic resin modified with 1.5% $ZrO_2$-NPs |
| | One layer; samples fabricated entirely from modified AR + Ag-NPs | | IAg 0.5% | Acrylic resin modified with 0.5% Ag-NPs |
| | | | IAg 1.0% | Acrylic resin modified with 1.0% Ag-NPs |
| | | | IAg 1.5% | Acrylic resin modified with 1.5% Ag-NPs |
| (Group II) Two Layers | First layer is fabricated from unmodified AR while superficial layer is fabricated from modified AR + $ZrO_2$-NPs | | IIZr 0.5% | Acrylic resin modified with 0.5% $ZrO_2$-NPs |
| | | | IIZr 1.0% | Acrylic resin modified with 1.0% $ZrO_2$-NPs |
| | | | IIZr 1.5% | Acrylic resin modified with 1.5% $ZrO_2$-NPs |
| | First layer is fabricated from unmodified AR while superficial layer is fabricated from modified AR + Ag-NPs | | IIAg 0.5% | Acrylic resin modified with 0.5% Ag-NPs |
| | | | IIAg 1.0% | Acrylic resin modified with 1.0% Ag-NPs |
| | | | IIAg 1.5% | Acrylic resin modified with 1.5% Ag-NPs |

AR: acrylic resin,
$ZrO_2$-NPs: zirconia nano-particles,
Ag-NPs: silver nano-particles Pure (unmodified) denture base acrylic resin packed into one layer was used as a control. The treatment and addition of zirconia nano-particles ($ZrO_2$-NPs) and silver nano-particles (Ag-NPs) were done according procedures described in *J Mater. Sci.* Technol. 2014, 30, 782-790, *Int J. Nanomed.* 2016, 11, 5633-5643, *Gerodontology* 2016, 33, 209-216, and *J Appl. Microbiol.* 2012, 112, 1163-72, each of which is incorporated by reference in its entirety herein. Essentially, silanized zirconia nano-particles ($ZrO_2$-NPs) and silver nano-particles (Ag-NPs) were added to acrylic resin powder (Major base 20, Major Prodotti Dentari, SPA, Italy) and thoroughly mixed, homogenized in a ball mill for 8 hours to create denture base acrylic resins containing nano-fillers at final concentrations of 0.5, 1.0, and 1.5% (w/w). The nano-fillers were added separately to denture base acrylic resin. According to manufacturer instruction, the prepared acrylic polymer and monomer were mixed in proportion of 5 g polymer to 3.5 mL monomer. The mixture was packed into mold spaces in a viscous, dough-like phase.

Figure 2:
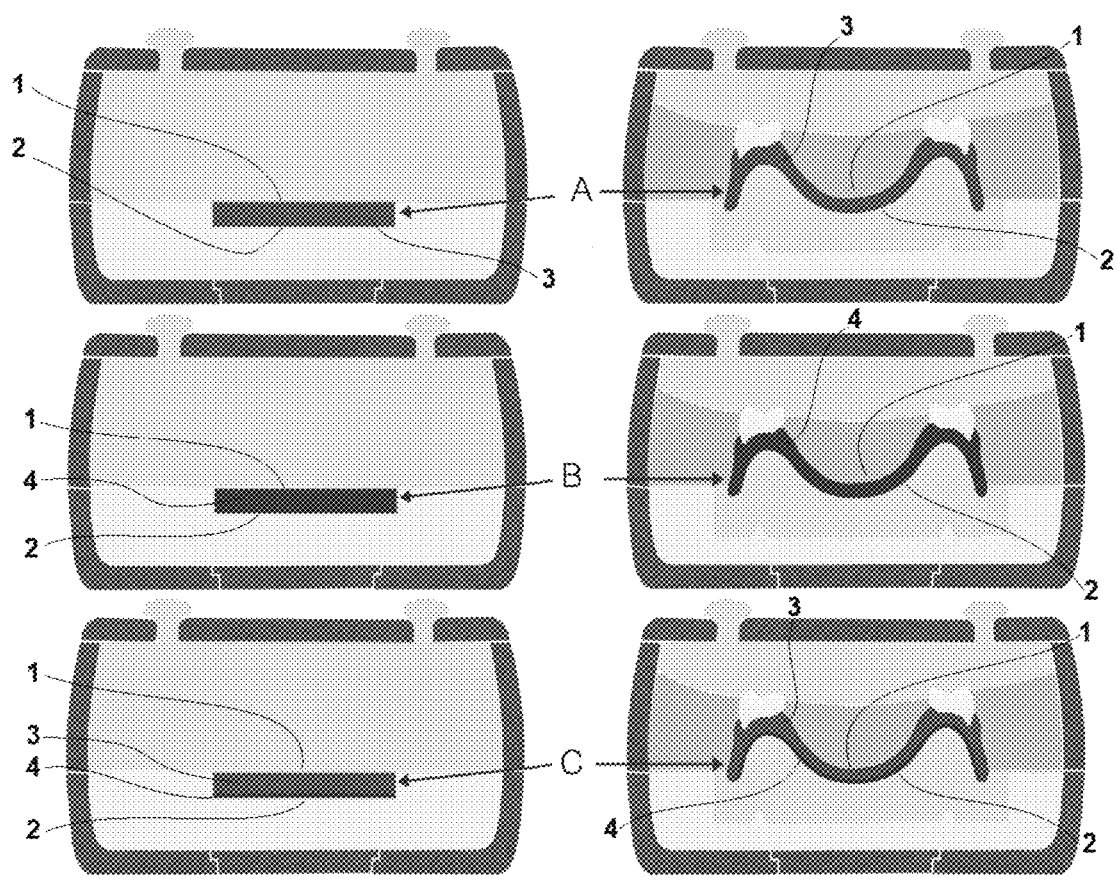
FIG. 2 shows schematic representations of the sample design in the study on the left panel, with denture base with layers (right panel), with an upper row (A) illustrating a one-layer control having unmodified heat-polymerized acrylic resin, a middle row (B) illustration a Group I—one-layer sample made completely of modified heat-polymerized acrylic resin, and a lower row (C) illustrating a Group II—two-layer sample made of unmodified heat-polymerized acrylic resin on a cameo surface and lined with modified heat-polymerized acrylic resin at intaglio surface.

For one-layer samples (Group I), the control group contained an unmodified acrylic resin, as indicated at the top (A) of FIG. 2, while samples modified with zirconia nanoparticles (ZrO$_2$-NPs) and silver nano-particles (Ag-NPs) contained the respective concentration of filler(s) packed in one step, as seen in the middle (B) of FIG. 2. In two-layer samples (Group II), two mixes were prepared, one of the unmodified acrylic resin and the second of nano-filler modified acrylic resins, as seen at the bottom (C) of FIG. 2.

Both types of resin, i.e., an additive-free resin composition and ZrO$_2$ or Ag-loaded resin composition, were mixed, 15 seconds apart, starting with the unmodified acrylic resin (additive-free resin composition). The compositions were left to the side to reach the viscous, dough-like stage. The first layer was packed against the cameo surface using unmodified acrylic resin, then covered with two layers of aluminum foil (total of 0.4 mm in thickness), cut in the same dimensions of the sample, followed by a wet, clear cellophane separating sheet. A wet cellophane sheet was used as a separating medium between the stone and the acrylic resin during the trial closure under a load of 8335.65 N in a pneumatic press. At the time, nano-filler modified acrylic resin in the viscous, dough-like stage was rolled out in a thin film between two wet cellophane sheets.

The flask/form was opened, cellophane and aluminum foil sheets were removed, and excess acrylic was trimmed. Following removal of the cellophane and aluminum foil sheets, the modified acrylic resin was introduced at the intaglio side of the flask/form before reassembling. The final compression of the samples was achieved using a pneumatic press for 5 minutes at 12258.31 N.

The flask/form was then placed in the flask/form frame for 30 minutes prior to polymerization. The flask/form frame was placed into a KaVo thermally controlled curing unit from the Elektrotechnisches Werk GmbH (Leutkirch, Germany) at room temperature and processed for 8 hours at 74° C., followed by 1 hour at 100° C. After polymerization, the samples were retrieved and finished, whereby excess resin was trimmed away using an HM 79GX-040 HP tungsten carbide bur from Meisinger (Centennial, Colo.) at 18,000 rpm followed by FINOPOL Polishers fine cylindrical silicon tips from LABOSHOP GmbH (Germany).

Employing the conventional method of denture fabrication, only the cameo surface was polished, leaving the intaglio surface with a nano-filler layer unpolished. For the final polishing, a Metaserve 250 grinder-polisher mechanical polishing machine from Buehler (Lake Bluff, Ill.) fitted with a TexMet C10in 42-3210 polishing cloth disc and Master Prep polishing suspension (0.05 µm) each from Buehler GmbH (Dusseldorf, Germany), operated at 100 rpm for 2 minutes under wet conditions. Sample dimensions were confirmed using a Neiko 01407A digital caliper with 0.01 mm accuracy from Neiko Tools US (LaPorte, Ind.). Conforming samples were kept in distilled water at 37° C. for 1 week prior to testing.

Testing Procedures

*C. albicans* Adherence Assay: The samples were sterilized with 70% ethanol, then cleaned ultrasonically with sterilized distilled water. The sterilized samples were soaked in artificial saliva (A. S. Orthana of Biofac A/S, Kastrup, Denmark) containing 2,000,000 cells of *Candida albicans* (ATCC 10231) at 37° C. for 48 hours. To detach non-adherent cells, phosphate-buffered saline (PBS) was used to wash the acrylic samples three times. The samples were then put in sterile tubes containing 1 mL of Sabouraud's dextrose broth (SDB-Acumedica Co., Manufacturers, Inc.) for 24 hours. After that the samples were vibrated for 10 minutes with a vortex mixer. To obtain clustered pellets of *C. albicans*, the tubes were then centrifuged five minutes at 4500 rpm. The acrylic resin samples were extracted from the tubes after being centrifuged, and the clustered pellets were collected. The *Candida albicans* attached to each sample was counted by two methods, based on J. Prosthodont. 2013, 22, 445-50 and *Int. J Nanomed.* 2017, 12, 5409, each of which is incorporated by reference herein in its entirety, and are summarized below.

The slide count method (Neubauer) for microscopic evaluation: 2.5 µL of 0.4% Trypan Blue solution in phosphate (MP-Biomedicals) were added to 7.5 µL of each concentrated *Candida* pellet and positioned on a slide worktable (Neubauer Slide Counter; Chambers-Marienfeld). The Trypan Blue stain distinguishes the living *C. albicans* form the dead. The living *C. albicans* cells will appear transparent and surrounded by blue borderline, while the dead cells will be colored blue. *C. albicans* cells were counted using light microscope at 10× magnification. Each slide was divided into four main squares; and each large square was further divided into 16 smaller ones. *C. albicans* cells were counted in two main squares, then multiplied by two to achieve the total *Candida* count.

The direct culture method involving a colony forming unit (CFU): 10 µL of each isolated centrifuged pellet were spread on a petri dish and incubated for 24 hours at 37° C. A marker pen counter (Colony counter from SP Scienceware, Bel-Art Products) was used to count the *C. albicans* colonies. The number of colonies was calibrated for the dilution used. The *Candida* was considered in a state of overgrowth with the number of colonies reached 5000 or more.

Flexural Strength Test

A three-point bending test was performed after removal of samples from the distilled water, without drying, using an Instron Model 2519-106 universal testing machine from Norwood, Mass., USA. Samples were supported by two stainless-steel supports, 50 mm apart. The load was applied at the midpoint of intaglio surface of the samples using a 5 kN load cell and blunt round end tip of 2 mm diameter at a crosshead speed of 5 mm per minute. The maximum load at fracture was noted, and the flexural strength of each sample was calculated using the Equation 1:

$$\text{flexural strength } (FS) = \frac{3WL}{2bd^2}, \quad \text{Eq. 1}$$

wherein the flexural strength is in MPa, W is the maximum load at fracture in Newtons (N), L is the distance between the supports, i.e., 50 mm, b is the sample width, i.e., 10 mm, and d is the sample thickness, i.e., 2.5 mm.

Scanning Electron Microscopy (SEM)

To study the nature of fracture and distribution of nano-fillers inside the polymer matrix, the fractured surfaces were evaluated using an FEI Inspect S50 scanning electron microscope (SEM). The samples were sputter coated with a Quorum Q150R ES device (UK), and scanned at 20 kV with a working distance of approximately 10 mm. The electronic images were captured at various magnifications to analyze relevant features of the samples and determine the nature of failure. For better comparison between different samples, the electronic images are presented at the same magnifications.

Fourier-Transform Infrared Spectroscopy (FTIR)

A Thermo Fisher Scientific Nicolet 6700 fourier-transform infrared (FTIR) spectroscope (USA) was used to identify the type of bonding formed in the PMMA matrix after polymerization optionally in the presence of nano-fillers, i.e., zirconia nano-particles (ZrO$_2$-NPs) and/or silver nano-particles (Ag-NPs). The FTIR spectra were recorded between 4000 and 400 cm⁻¹, i.e., the entire range of infra-red spectrum. For comparison, a spectrum of pure PMMA was also obtained.

Translucency

An X-Rite COLOR-EYE® 7000A spectrophotometer was used to measure the reflectance values of samples. Small aperture viewing area, i.e., 10×7.5 mm, was used. The spectrophotometer was calibrated first using the supplied white tile and black trap, then a sample was placed against the port and supported by a white or black reference material before closing the support arm. Measurements of the three-color coordinates of the Commission Internationale de l'Eclairage (CIE L*a*b*) system were undertaken for each sample against each background. The average value was automatically calculated by the software from three measurements. The data was tabulated and the translucency value was determined using Equation 2:

$$TR=[(L^*_{white}-L^*_{black})^2+(a^*_{white}-a^*_{black})^2+(b^*_{white}-b^*_{black})^2]^{1/2} \quad \text{Eq. 2,}$$

wherein TR is the translucency.

Surface Roughness

A Bruker Nano Contour Gt-K1 optical profiler non-contact optical interferometric profilometer (Tucson, Ariz., USA) was used to measure the surface roughness ($R_a$, μm) of each sample following the same method described by *Dent. Mater. J.* 2018, 30, 746-753, which is incorporated by reference herein in its entirety. Each sample was measured three times, and an average reading was calculated and noted as the $R_a$ value of that sample.

Primary Statistical Analysis

Three-way ANOVA and Tukey post hoc tests were used to identify statistical differences among groups ($\alpha=0.05$). For the *C. albicans* count using the slide count method, the 3-way ANOVA showed the number of layers, type, or concentration of nanofiller, and the combined effect of the last 2 variables were all significant (P<0.05) as seen in Table 2.

TABLE 2

| Three-way ANOVA for Candida count (slide count) | | | | | |
|---|---|---|---|---|---|
| Source of Variation | Sum of Square | df | Mean Square | F | P |
| Concentration | 3621455.117 | 2 | 1810727.558 | 2061.445 | <.0001* |
| Layer | 3876.033 | 1 | 3876.033 | 4.413 | 0.038* |
| Nanofiller | 5336613.633 | 1 | 5336613.633 | 6075.534 | <0.001* |
| Concentration × Layer | 277.117 | 2 | 138.558 | 0.158 | 0.854 |
| Concentration × Nanofiller | 716258.617 | 2 | 358129.308 | 407.717 | <0.001* |
| Layer × Nanofiller | 104.533 | 1 | 104.533 | 0.119 | 0.731 |
| Concentration × Layer × Nanofiller | 1390.017 | 2 | 695.008 | 0.791 | 0.456 |
| Error | 94864.800 | 108 | 878.378 | | |
| Total | 28321298.000 | 120 | | | |
| Corrected Total | 9774839.867 | 119 | | | |

*statistically significant (P < 0.05)

However, all factors were significant for the *C. albicans* count using the direct culture method except the combined effect of all 3 factors (P=0.083) as seen in Table 3.

TABLE 3

| Three-way ANOVA for *Candida* count (direct culture) | | | | | |
|---|---|---|---|---|---|
| Source of Variation | Sum of Square | df | Mean Square | F | P |
| Concentration | 8224304.217 | 2 | 4112152.108 | 2569.976 | <0.001* |
| Layer | 36470.533 | 1 | 36470.533 | 22.793 | <0.001* |
| Nanofiller | 9005832.300 | 1 | 9005832.300 | 5628.385 | <0.001* |
| Concentration × Layer | 10469.117 | 2 | 5234.558 | 3.271 | 0.042* |
| Concentration × Nanofiller | 34315.850 | 2 | 17157.925 | 10.723 | <0.001* |
| Layer × Nanofiller | 11368.533 | 1 | 11368.533 | 7.105 | 0.009* |
| Concentration × Layer × Nanofiller | 8165.417 | 2 | 4082.708 | 2.552 | 0.083 |
| Error | 172808.000 | 108 | 1600.074 | | |
| Total | 154502530.000 | 120 | | | |
| Corrected Total | 17503733.967 | 119 | | | |

*statistically significant (P < 0.05)

In both counting methods, the *C. albicans* count significantly decreased with both fillers in the 1- or 2-layer techniques compared with the control group (P<0.001) as seen in Table 4.

TABLE 4

Mean ± standard deviation and statistical significance of *Candida* count (CFU/mL) for all specimens

| | Groups | | | |
|---|---|---|---|---|
| | Slide Count | | Direct Culture | |
| | Control | | | |
| | 2035.9 ± 134.0 | | 3602.0 ± 339.3 | |
| | Layers | | | |
| | I | II | I | II |
| Zr 0.5% | 942.4 ± 37.4 | 942.8 ± 14.6 | 1658.6 ± 39.0 | 1665.5 ± 41.7 |
| Zr 1.0% | 536.2 ± 41.4 | 517.1 ± 40.6 | 1318.6 ± 70.7 | 1385.7 ± 37.4 |
| Zr 1.5% | 353.3 ± 43.1 $^a$ | 332.3 ± 29.0 $^a$ | 968.6 ± 32.0 $^a$ | 1057.6 ± 36.6 $^a$ |
| Ag 0.5% | 322.4 ± 35.5 $^a$ | 373.2 ± 18.0 $^a$ | 1075.6 ± 30.0 $^a$ | 1085.9 ± 24.2 $^a$ |
| Ag 1.0% | 147.2 ± 31.7 $^b$ | 142.2 ± 21.8 | 838.6 ± 40.8 | 862.6 ± 36.2 |
| Ag 1.5% | 91.4 ± 7.1 $^b$ | 83.0 ± 2.9 | 446.3 ± 37.4 | 458.2 ± 36.4 |

Zr: zirconium dioxide nanoparticles;
Ag: silver nanoparticles;
I: 1-layer;
II: 2-layers
Vertically, identical superscripted lowercase letters denote no significant differences among groups per count method and per nanoparticles (P > 0.05).
Horizontally, no significant differences between I and II per respective concentration or counting method detected.

With regard to flexural strength, as seen in Table 5, the 3-way ANOVA showed that the number of layers and type of nano-filler resulted in significant differences; however, the concentration was not significant (P=0.186).

TABLE 5

Three-way ANOVA for flexural strength

| Source of Variation | Sum of Square | df | Mean Square | F | P |
|---|---|---|---|---|---|
| Concentration | 6.475 | 2 | 3.238 | 1.708 | 0.186 |
| Layer | 266.859 | 1 | 266.859 | 140.745 | <0.001* |
| Nanofiller | 9233.583 | 1 | 9233.583 | 4869.924 | <0.001* |
| Concentration × Layer | 110.108 | 2 | 55.054 | 29.036 | <0.001* |
| Concentration × Nanofiller | 1119.898 | 2 | 559.949 | 295.325 | <0.001* |
| Layer × Nanofiller | 2172.688 | 1 | 2172.688 | 1145.907 | <0.001* |
| Concentration × Layer × Nanofiller | 434.690 | 2 | 217.345 | 114.631 | <0.001* |
| Error | 204.773 | 108 | 1.896 | | |
| Total | 840014.949 | 120 | | | |
| Corrected Total | 13549.075 | 119 | | | |

*statistically significant (P < 0.05)

Additionally, all interactions at the level of 2 or 3 factors were significant (P<0.001). Zirconia nano-particles ($ZrO_2$-NPs) in 1 or 2 layers can significantly increase the flexural strength in comparison with the control (P<0.001), as seen in Table 6.

TABLE 6

Mean ± standard deviation, and statistical significance of flexural strength (MPa), surface roughness (μm), and translucency for all tested specimens

| | Flexural Strength | | Surface Roughness | | Translucency | |
|---|---|---|---|---|---|---|
| Groups | I | II | I | II | I | II |
| Control | 80.7 ± 1.7 | 80.7 ± 1.7$^a$ | 0.16 ± 0.01$^a$ | 0.16 ± 0.01$^a$ | 14.4 ± 0.93 | 14.4 ± 0.93$^a$ |
| Zr 0.5% | 89.1 ± 1.4$^A$ | 86.4 ± 1.3$^A$ | 0.15 ± 0.01$^{a, A}$ | 0.14 ± 0.01$^{a, A}$ | 6.7 ± 0.55 | 12.8 ± 0.61$^{a, b}$ |

TABLE 6-continued

Mean ± standard deviation, and statistical significance of flexural strength
(MPa), surface roughness (μm), and translucency for all tested specimens

| Groups | Flexural Strength | | Surface Roughness | | Translucency | |
|---|---|---|---|---|---|---|
| | I | II | I | II | I | II |
| Zr 1.0% | 95.5 ± 1.2 | 88.7 ± 1.1 | 0.14 ± 0.01[a, B] | 0.14 ± 0.01[a, B] | 3.3 ± 0.35[a] | 11.3 ± 056[b] |
| Zr 1.5% | 99.0 ± 1.4 | 91.9 ± 1.4 | 0.17 ± 0.0[a, C] | 0.16 ± 0.01[a, C] | 2.9 ± 0.30[a] | 10.1 ± 0.62[b] |
| Ag 0.5% | 76.3 ± 0.9 | 80.2 ± 1.9[a] | 0.17 ± 0.01[a, D] | 0.19 ± 0.01[D] | 3.5 ± 0.20[a] | 6.90 ± 0.51 |
| Ag 1.0% | 66.6 ± 1.2 | 79.8 ± 1.7[a] | 0.26 ± 0.01[E] | 0.24 ± 0.01[E] | 2.6 ± 0.45[a] | 4.5 ± 0.24[c] |
| Ag 1.5% | 62.3 ± 1.3 | 79.9 ± 1.4[a] | 0.36 ± 0.01[F] | 0.34 ± 0.01[F] | 2.2 ± 0.32[a] | 3.4 ± 0.30[c] |

Zr: zirconium dioxide nanoparticles; Ag: silver nanoparticles; I: 1-layer; II,: 2-layers
Vertically, identical superscripted lowercase letters denote no significant differences among groups per count method and per nanoparticles ($P > 0.05$).
Horizontally, identical superscripted uppercase letters denote no significant differences between I and II per respective concentration ($P > 0.05$).

Silver nano-particle (Ag-NP) addition can decrease flexural strength significantly in 1-layer specimens and may not differ from the control or from each other in the 2 layer specimens ($P>0.05$). Comparing the same nano-filler concentration between the 1- and 2-layer specimens may show a significant reduction in flexural strength for all zirconia nano-particle ($ZrO_2$-NP) groups, as the number of layers increased except for Zr 0.5% ($P=0.576$). However, silver nano-particles (Ag-NPs) can show significantly higher flexural strength values in the 2-layer groups compared with the 1-layer groups for all concentrations ($P<0.05$).

The means and standard deviation of $R_a$ for all nanofiller samples and layers are shown in Table 6. The results of 3-way ANOVA showed that all 3 factors and all interactions produced significant results ($P<0.001$), except the combined effect of filler and layers ($P=0.059$), as seen in Table 7.

TABLE 7

Three-way ANOVA for surface roughness

| Source of Variation | Sum of Square | df | Mean Square | F | P |
|---|---|---|---|---|---|
| Concentration | 0.198 | 2 | 0.099 | 1205.656 | <0.001* |
| Layer | 0.001 | 1 | 0.001 | 15.398 | <0.001* |
| Nanofiller | 0.389 | 1 | 0.389 | 4722.611 | <0.001* |
| Concentration × Layer | 0.002 | 2 | 0.001 | 12.148 | <0.001* |
| Concentration × Nanofiller | 0.119 | 2 | 0.059 | 720.445 | <0.001* |
| Layer × Nanofiller | 0.000 | 1 | 0.000 | 3.655 | 0.059 |
| Concentration × Layer × Nanofiller | 0.004 | 2 | 0.002 | 22.515 | <0.001* |
| Error | 0.009 | 108 | 8.231E−5 | | |
| Total | 5.769 | 120 | | | |
| Corrected Total | 0.722 | 119 | | | |

*statistically significant ($P < 0.05$)

Considering nano-filler type, the addition of zirconia nano-particles ($ZrO_2$-NPs) in 1 or 2 layers did not affect $R_a$ ($P>0.05$) in contrast with silver nano-particles (Ag-NPs) which significantly increased $R_a$ in the 1- or 2-layer specimens ($P<0.001$), except (I Ag 0.5*) ($P=0.955$).

Exemplary mean and standard deviation values of translucency (TR) are presented in Table 6A. The 3-way ANOVA results indicated that all 3 factors and their combined effect had significant results ($P<0.001$) except the interaction between filler type and concentration ($P=0.524$), as seen in Table 8.

TABLE 8

Three-way ANOVA for translucency

| Source of Variation | Sum of Square | df | Mean Square | F | P |
|---|---|---|---|---|---|
| Concentration | 151.879 | 2 | 75.940 | 387.720 | <0.001* |
| Layer | 565.763 | 1 | 565.763 | 2888.580 | <0.001* |
| Nanofiller | 576.058 | 1 | 576.058 | 2941.143 | <0.001* |
| Concentration × Layer | 0.255 | 2 | 0.127 | .651 | 0.524 |

TABLE 8-continued

Three-way ANOVA for translucency

| Source of Variation | Sum of Square | df | Mean Square | F | P |
|---|---|---|---|---|---|
| Concentration × Nanofiller | 7.971 | 2 | 3.986 | 20.350 | <0.001* |
| Layer × Nanofiller | 232.186 | 1 | 232.186 | 1185.457 | <0.001* |
| Concentration × Layer × Nanofiller | 14.727 | 2 | 7.364 | 37.596 | <0.001* |
| Error | 21.153 | 108 | .196 | | |
| Total | 5441.026 | 120 | | | |
| Corrected Total | 1569.992 | 119 | | | |

*statistically significant (P < 0.05)

For 1 layer, all additions decreased the translucency significantly (P<0.001). Similar results were found with 2-layer specimens except (II Zr 0.5%) which showed the highest translucency value (12.8±0.61) among all modified groups, matching that of the control. Comparison between 1- and 2-layer modified specimens may indicate that both fillers in all concentrations showed significantly higher (P<0.05) translucency values for 2-layer groups, as seen in Table 6A.

Figure 3:
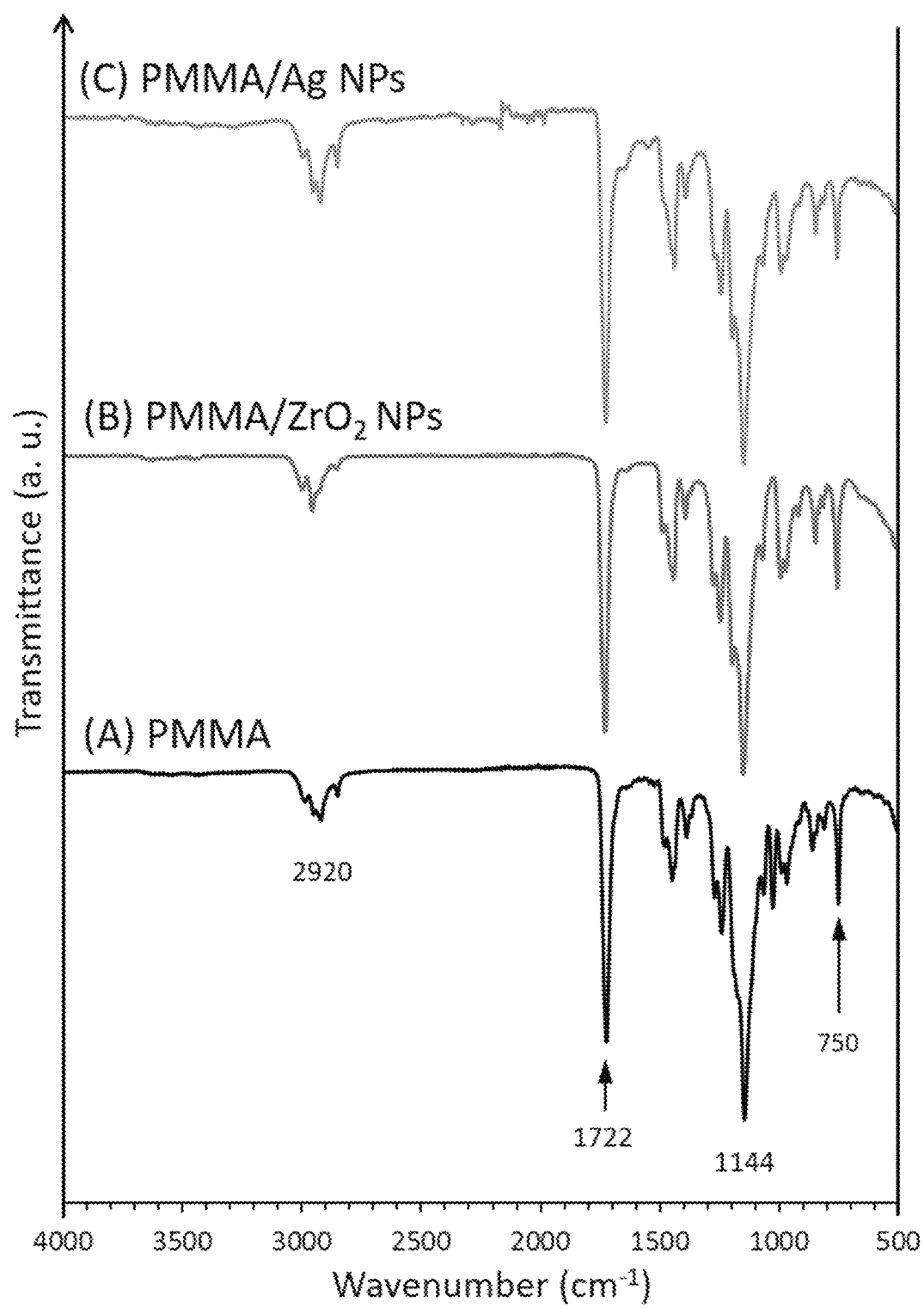
FIG. 3 shows Fourier-transform infrared (FTIR) spectra of (A) pure PMMA, (B) PMMA including zirconia nano-particles ($ZrO_2$-NPs), and (C) PMMA including silver nano-particles (Ag-NPs), between 4000-500 $cm^{-1}$.

The results of Fourier-transform infrared (FTIR) analysis for pure and modified PMMA are shown in FIG. 3. All FTIR spectra showed the same kind of bands and characteristic features of PMMA, confirming that the incorporation of nanofillers did not affect the structure of the PMMA chain. The SEM analysis for exemplary 2-layer denture base materials displayed a distinct interface between the 2 layers as seen in FIG. 4 for zirconia nano-particles ($ZrO_2$-NPs) and silver nano-particles (Ag-NPs). FIG. 5 shows SEM images of the cluster formation of zirconia nano-particles ($ZrO_2$-NPs) and silver nano-particles (Ag-NPs).

The addition of $ZrO_2$ nanoparticles and Ag nanoparticles in the 1- or 2-layer specimens can reduce *Candida albicans* adhesion (P<0.001). In the 1- and 2-layer specimens, flexural strength can be significantly increased with zirconia nano-particles ($ZrO_2$-NPs). Silver nano-particles (Ag-NPs) can decrease flexural strength, particularly in the 1-layer specimen (P<0.001). Surface roughness may not be changed for the 1- and 2-layer specimens with zirconia nano-particles ($ZrO_2$-NPs) or the 1-layer specimen with 0.5% silver nano-particles (Ag-NPs) (P>0.05), while other silver nano-particle (Ag-NP) groups can exhibit increased surface roughness (P<0.001). Silver nano-particles (Ag-NPs) can be significantly lowered translucency in the 1- and 2-layer specimens (P<0.001), while zirconia nano-particles ($ZrO_2$-NPs) may decrease translucency only in the 1-layer specimen (P<0.001).

Secondary Statistical Analysis

IBM Corp. IBM SPSS Statistics 23 software (Armonk, N.Y.) was used for the following statistical analyses. Arithmetic means and standard deviations for categorized parameters were calculated. ANOVA and Tukey's post hoc tests were used at α=0.05. ANOVA was used to test the overall significance for all properties between all groups analyzed by Tukey's HSD post hoc test in the presence of a significant p-value.

The samples were tested for *C. albicans*, flexural strength, surface roughness, and translucency. The means, standard deviations, and statistical significances of *C. albicans* count, flexural strength, surface roughness, and translucency are summarized below in Tables 9 and 10.

TABLE 9

Mean (± standard deviations), and statistical significance of flexural strength (MPa), surface roughness (μm), and translucency for all tested samples.

| | Flexural Strength Mean ± SD | | Surface Roughness Mean ± SD | | Translucency Mean ± SD | |
|---|---|---|---|---|---|---|
| Groups | I | II | I | II | I | II |
| Control | 80.7 ± 1.7 | 80.7 ± 1.7$^a$ | 0.16 ± 0.01$^a$ | 0.16 ± 0.01$^a$ | 14.4 ± 0.93 | 14.4 ± 0.93$^a$ |
| Zr 0.5% | 89.1 ± 1.4$^A$ | 86.4 ± 1.3$^A$ | 0.15 ± 0.01$^{a, A}$ | 0.14 ± 0.01$^{a, A}$ | 6.7 ± 0.55 | 12.8 ± 0.61$^{a, b}$ |
| Zr 1.0% | 95.5 ± 1.2 | 88.7 ± 1.1 | 0.14 ± 0.01$^{a, B}$ | 0.14 ± 0.01$^{a, B}$ | 3.3 ± 0.35$^a$ | 11.3 ± 0.56$^b$ |
| Zr 1.5% | 99.0 ± 1.4 | 91.9 ± 1.4 | 0.17 ± 0.01$^{a, C}$ | 0.16 ± 0.01$^{a, C}$ | 2.9 ± 0.30$^a$ | 10.1 ± 0.62$^b$ |
| Ag 0.5% | 76.3 ± 0.9 | 80.2 ± 1.9$^a$ | 0.17 ± 0.01$^{a, D}$ | 0.19 ± 0.01$^D$ | 3.5 ± 0.20$^a$ | 6.9 ± 0.51 |
| Ag 1.0% | 66.8 ± 1.2 | 79.8 ± 1.7$^a$ | 0.26 ± 0.01$^E$ | 0.24 ± 0.01$^E$ | 2.6 ± 0.45$^a$ | 4.5 ± 0.24$^c$ |
| Ag 1.5% | 62.3 ± 1.3 | 79.9 ± 1.4$^a$ | 0.36 ± 0.01$^F$ | 0.34 ± 0.01$^F$ | 2.2 ± 0.32$^a$ | 3.4 ± 0.30$^c$ |

(Zr) zirconium oxide nanoparticles; (Ag) silver nanoparticles; (I) one layer; (II) two layers Vertically, identical superscripted small letters denote no significant differences among groups at p > 0.05.

Horizontally, identical superscripted capital letters denote no significant differences between I and II per respective concentration at p > 0.05.

TABLE 10

Means (± standard deviations) and statistical significance of *Candida* count for all samples.

| Groups | Slide Count Mean ± SD | | Direct Culture Mean ± SD | |
|---|---|---|---|---|
| | I | II | I | II |
| Control | 2035.9 ± 134.0 | — | 3602.0 ± 339.3 | — |
| Zr 0.5% | 942.4 ± 37.4 | 942.8 ± 14.6 | 1658.6 ± 39.0 | 1665.5 ± 41.7 |
| Zr 1.0% | 536.2 ± 41.4 | 517.1 ± 40.6 | 1318.6 ± 70.7 | 1385.7 ± 37.4 |
| Zr 1.5% | 353.3 ± 43.1$^a$ | 332.3 ± 29.0$^a$ | 968.6 ± 32.0$^a$ | 1057.6 ± 36.6$^a$ |
| Ag 0.5% | 322.4 ± 35.5$^a$ | 373.2 ± 18.0$^a$ | 1075.6 ± 30.0$^a$ | 1085.9 ± 24.2$^a$ |
| Ag 1.0% | 147.2 ± 31.7$^b$ | 142.2 ± 21.8 | 838.6 ± 40.8 | 862.6 ± 36.2 |
| Ag 1.5% | 91.4 ± 7.1$^b$ | 83.0 ± 2.9 | 446.3 ± 37.4 | 458.2 ± 36.4 |

(Zr) zirconium oxide nanoparticles;
(Ag) silver nanoparticles;
(I) one layer;
(II) two layers
Vertically, identical superscripted small letters denote no significant differences among groups at p > 0.05.
Horizontally, all groups are significantly different.

One-way ANOVA revealed that adding zirconia nano-particles ($ZrO_2$-NPs) and/or silver nano-particles (Ag-NPs) in one or two layers significantly decreased the *Candida* adhesion (F=1283.306, P<0.001) and (F=593.168, P<0.001) compared to control group, as seen in Table 9. Both methods, i.e., slide count test and direct culture test, show that, in comparison to control group, the *Candida* count decreased with either or both fillers in one-layer and two-layer techniques at P<0.001.

The reduction in the *Candida* count was found to be inversely related to the filler concentration for both types of fillers and the number of layers, and the lowest *Candida* count was recorded with silver nano-particles (Ag-NPs) 1.5 wt. % in Group I (91.4±7.1) and Group II (83.0±2.9). When comparing zirconia nano-particles ($ZrO_2$-NPs) and silver nano-particles (Ag-NPs), there were differences between all groups except, Group I, Zr wt. 1.5%, and Group I, Ag 0.5 wt. %, by slide count at P=0.91, and by direct culture at P=0.567, and Group II, Zr wt. 1.5% and Group II, Ag wt.0.5%, by slide count at P=0.175, and by direct culture at P=0.459.

One-way ANOVA revealed that zirconia nano-particle ($ZrO_2$-NP) and silver nano-particle (Ag-NP) addition in one-layer and two-layer acrylic resin bases affected the flexural strength (F=1096.350, P<0.001) for one-layer samples with zirconia nano-particles ($ZrO_2$-NPs) and (F=125.625, P<0.001) for two-layer samples with zirconia nano-particles ($ZrO_2$—NPs). Zirconia nano-particles ($ZrO_2$-NPs) in one-layer and two-layer increased the flexural strength in comparison to control group (p<0.001). The increase was directly proportional to the zirconia nano-particle ($ZrO_2$-NP) concentration with the highest flexural strength value for Group I, Zr 1.5 wt. %, of 99.00±1.4 MPa. Silver nano-particle (Ag-NP) addition in one-layer arrangements decreased the flexural strength compared to the control, whereby the lowest value obtained, with Group I, Ag 1.5 wt. %, was 62.3±1.3 MPa. Silver nano-particles (Ag-NPs) in two-layer denture bases did not significantly affect the flexural strength. There was no difference between control group and Ag-loaded Group II samples, nor between the Group II-Ag samples among themselves (p>0.05).

When comparing the same concentration of filler addition between one-layer samples, i.e., Group I, and two-layer samples, i.e., Group II, a reduction in flexural strength was detected for all zirconia nano-particle ($ZrO_2$-NP)-loaded samples, with loading in two-layer bases having lower values except for Group II Zr 0.5 wt. % (P=0.576). On the contrary, silver nano-particle (Ag-NP)-loaded samples showed higher flexural strength values in the two-layer samples compared to one-layer samples for all concentrations (P<0.05).

One-way ANOVA revealed that zirconia nano-particle ($ZrO_2$-NP) and silver nano-particle (Ag-NP) addition in one- and two-layers affected surface roughness (F=801.133, P=0.000) for one-layer samples with zirconia nano-particles ($ZrO_2$-NPs) and (F=754.746, P=0.000) for two-layer samples with zirconia nano-particles ($ZrO_2$-NPs). As shown in Table 10, above, no significant differences were found in surface roughness with the addition of zirconia nano-particles ($ZrO_2$-NPs) in one-layer versus two-layer arrangements compared to control group (p>0.05). In contrast, adding silver nano-particle (Ag-NP) in one-layer or two-layer arrangements increased the surface roughness in comparison to control group (P<0.001), except in the case of Group I Ag 0.5 wt. % (P=0.955), which showed the lowest $R_a$ value among silver nano-particle (Ag-NP)-reinforced groups to be 0.17±0.01 μm for Ag 0.5 wt. %. Filler addition could not be determined to play a significant role in surface roughness between Groups I and II, i.e., one-layer and two-layer acrylic samples for all concentrations of zirconia nano-particles ($ZrO_2$-NPs) and silver nano-particles (Ag-NPs) (P<0.05).

One-way ANOVA revealed that addition of zirconia nano-particles ($ZrO_2$-NPs) and silver nano-particles (Ag-NPs) in one-layer and two-layer arrangements affected the translucency (F=902.470, P=0.000) and (F=688.719, P=0.000), respectively. The addition of zirconia nano-particles ($ZrO_2$-NPs) and/or silver nano-particles (Ag-NPs) in one-layer arrangements decreased the translucency in comparison to control group (p<0.001). Regarding two-layer groups, there were differences between all groups and the control (p<0.001) except for Group II Zr 0.5 wt. %, which showed the highest translucency value, i.e., 12.8±0.61, among all modified samples. Between modified one-layer groups, no significant differences between all groups (p>0.05) were found except for Group I Zr 0.5 wt. %, which showed the highest translucency value, i.e., 6.7±0.55). For two-layer groups, no significant differences were detected between the zirconia nano-particle ($ZrO_2$-NP) subgroups (p>0.05), with Group II Zr 1.5 wt. % showing the lowest translucency value of 10.1±0.62. Additionally, a reduction in translucency was detected for Group II silver nano-particle (Ag-NP) subgroups with no difference between Group II Ag 1.0 and 1.5 wt. %) (P=0.966) with Group II Ag 0.5 wt. % having the highest translucency value, at 6.9±0.51.

The results of the comparison between one- and two-layer modified samples regarding translucency, showed that both fillers, zirconia nano-particles ($ZrO_2$-NPs) and silver nano-particles (Ag-NPs), in all three concentrations, i.e., 0.5, 1.0, and 1.5 wt. %, showed increases (P<0.05) in translucency values for the two-layer samples compared to one-layer samples, with Group I Ag 1.5 wt. % having the lowest translucency value among all modified samples.

Aspects of the invention include dentures with antimicrobial properties, beneficial to denture wearers. Antifungal agent addition on an intaglio surface of the denture may reduce the expected negative effects of added fillers on the overall performance of final nano-composite denture. Aspects of the invention provide little to no difference in *Candida* adhesion between one-layer and two-layer modified denture bases. The fabrication of one-layer or two-layer modified denture bases can affect few properties of the acrylic resin.

The adherence of *C. albicans* to denture base acrylic resin may be determined by counting viable microorganisms (CFU on plates) and/or slide count method (Neubaur). Both nano-fillers, zirconia nano-particles ($ZrO_2$-NPs) and silver nano-particles (Ag-NPs), either in one- or two-layers showed similar behaviors against *Candida* adhesion. In both methods, the *Candida* count declined as the zirconia nano-particles ($ZrO_2$-NPs) and silver nano-particles (Ag-NPs) concentration increased and the lowest *Candida* count was found with 1.5 wt. % of both nano-fillers. The silver nano-particles (Ag-NPs) showed larger reduction in *Candida* count than zirconia nano-particles ($ZrO_2$-NPs). The decrease noted may be related to the antifungal effect of both nano-fillers. The addition in one-layer or two-layer arrangements resulted in similar *Candida* adhesion levels. However, a two-layer denture base is preferable to one-layer structures, as the two-layer arrangement can overcome the negative effects of extensive amount of nano-fillers through the whole denture base matrix.

Silver nano-particles (Ag-NPs) wrap around *Candida* cells and cause membrane disruption and inhibition of normal budding process. Silver ions in the PMMA matrix are freed into the surrounding medium to perform their antifungal activity. The nano-silver with its rapid and broad-spectrum efficacy in addition to the continuous release of silver ions appear to provide an antimicrobial effect. The nano-silver particles can be sensitive to oxygen and can convert $O_2$ into active mode by catalytic action. The oxygen in its active form can cause structural damage to microorganisms. Silver ions are positively charged, interacting with negatively charged cell membrane of the *Candida* to bring about increased cell wall permeability and death. Silver also adheres to *Candida* DNA, RNA, proteins, and enzymes, preventing cell division and damaging cellular content.

The antimicrobial activity of zirconia nano-particles ($ZrO_2$-NPs) to activating oxygen species can likewise disturb microorganismic cell membranes. During this process, there can be an increase in cell membrane permeability, triggering zirconia nano-particle ($ZrO_2$-NP) accumulation within the membrane and cytoplasm of the microorganism.

In one-layer denture bases where zirconia nano-particles ($ZrO_2$-NPs) were on all surfaces and within the denture base, or in two-layer denture bases where zirconia nano-particles ($ZrO_2$-NPs) were only present at the superficial intaglio surface, significant increases in flexural strength were noted compared to unmodified denture base, and these increases were proportional to the zirconia nano-particle ($ZrO_2$-NP) concentration. The flexural strength increases may be attributed to the fact that zirconia nano-particles ($ZrO_2$-NPs) possess inherent characteristics enabling them to improve the mechanical properties of modified acrylic base.

However, a reduction in flexural strength was observed with the two-layers compared to the respective concentration in one-layer denture base. The reduction in flexural strength may be linked to an absence of zirconia nano-particles ($ZrO_2$-NPs) through the whole denture base, from cameo surface to the interface between pure acrylic, and the modified layer at the intaglio surface, allowing cracks to initiate at the cameo surface and propagate without interference until it is arrested by zirconia nano-particles ($ZrO_2$-NPs) at the intaglio surface resulting in a degree of flexural strength improvement.

The flexural strength was reduced more significantly if silver nano-particles (Ag-NPs) were added in one-layer than two-layer denture bases. In one-layer arrangements, the addition of silver nano-particles (Ag-NPs) decreased flexural strength directly proportionally to silver nano-particle (Ag-NP) concentration, with the lowest flexural strength value recorded for one-layer 1.5 wt. % silver nano-particle (Ag-NP)-modified bases.

However, the flexural strength of silver nano-particle (Ag-NP)-loaded samples used in this study were found to exceed the value recommended by ISO 20795-1:2008 (ISO, 2008) for flexural strength of polymeric materials (65 MPa) except one-layer 1.5%-Ag-NPs modified bases. A gradual reduction in flexural strength was observed in silver nano-particle (Ag-NP)-modified one-layer samples from 0.5 to 1.5 wt. %. This decrease in flexural strength may be explained based on that the increase of silver nano-particle (Ag-NP) concentration reduced its interaction with the polymer, leading to structural disorder of the nano-composite and reduction of mechanical strength.

On the other hand, in two-layers, silver nano-particle (Ag-NP) addition did not show changes in flexural strength in comparison to the control. The weak effect in two-layer, silver nano-particle (Ag-NP)-loaded samples may be explained by the reduced amount of silver nano-particles (Ag-NPs) limiting particle presence to a thin layer at intaglio surface. Double layering may be useful with antifungal agents that may otherwise adversely affect the denture properties if added in one-layer denture base.

The addition of zirconia nano-particles ($ZrO_2$-NPs) either in one-layer or two-layer denture base samples did not change surface roughness ($R_a$). Moreover, all $R_a$ values for samples containing zirconia nano-particles ($ZrO_2$-NPs) were within the clinically acceptable value of 0.2 µm, above which the surface is prone to more *Candida* adhesion and color change. The addition of silver nano-particles (Ag-NPs) in one-layer or two-layer denture base samples, however, increased $R_a$ values above the clinically acceptable value except for 0.5 wt. % Ag. Although high $R_a$ values were recorded, these groups showed an intense antimicrobial effect reflecting the role of silver nano-particles (Ag-NPs) as antifungal agents. The $R_a$ increase for samples containing silver nano-particles (Ag-NPs) may be attributed to the weakly attached silver nano-particles (Ag-NPs) on the denture surface which can easily be freed from acrylic resins. Contrarily, the good bonding between zirconia nano-particles ($ZrO_2$-NPs) and the polymer matrix may have prevented their separation, and consequently resulted in acceptable $R_a$ values.

Good optical properties of PMMA dentures are vital. The nature of PMMA allows it to accept filler reinforcement that may alter the optical properties and, consequently, the aesthetic results of the denture. For one-layer denture base samples, it was found that the addition of zirconia nano-particles ($ZrO_2$-NPs) and/or silver nano-particles (Ag-NPs) decreased the translucency of the modified samples in a direct relation with filler concentration.

Silver nano-particles (Ag-NPs) samples showed lower translucency values compared to zirconia nano-particles ($ZrO_2$-NPs) samples per respective concentration. This finding could be attributed to the gray color of silver nano-particles (Ag-NPs) compared to the white color of zirconia nano-particles ($ZrO_2$-NPs) samples. The effect on translucency may also be linked to inherent differences in optical properties of the fillers and their degree of dispersion within the resin matrix.

Zirconia nano-particles ($ZrO_2$-NPs) typically absorb more light due to their crystalline nature making them highly opaque. Clustering of zirconia nano-particles ($ZrO_2$-NPs) may also prevent light transmission, thereby decreasing translucency. Additional reflection of light at the filler/matrix interface may be caused by the difference in refractive indices between the two materials. The refractive index of zirconia nano-particles ($ZrO_2$-NPs), 2.1750, is higher than that of the PMMA, 1.4813. Since the exemplary nano-composites comprised organic resin and inorganic nano-particles, the higher the refractive index difference between the two phases, the greater the opacity of the nano-composite.

Previous studies have indicated that PMMA/silver nano-composites containing less than 0.25 wt. % Ag have translucency sufficient for use. For two-layer denture bases, a dramatic, unexpected improvement in the translucency was observed compared to one-layer denture bases, especially with zirconia nano-particles ($ZrO_2$-NPs). This translucency improvement may be attributed to the lower amount of nano-filler(s), in addition to the presence of nano-filler(s) in a thin layer at the intaglio surface.

Inventive two-layer denture bases, from a clinical point of view, offer a promising technique for denture base fabrication. Inventive two-layer denture bases may open the gate for antifungal agent incorporation, which could otherwise affect the properties of a denture base if added in larger amounts. Aspects of the invention may account for oral fluid, masticatory stress, irregular shape, and denture base configuration in operation.

Referring now to the drawings, wherein like reference numerals designate identical or corresponding parts throughout the several views.

FIG. 1A show a transmission electron microscopy (TEM) image of zirconia nano-particles ($ZrO_2$-NPs) used in the Examples. FIG. 1B shows a selected area (electron) diffraction (SAD or SAED) TEM image of the zirconia nano-particles ($ZrO_2$-NPs) used in the Examples. The electron diffraction patterns indicate a crystalline nature of the nano-particles, displaying near spherical shape. FIG. 1C shows a plot and chart of the particle size distribution of the zirconia nano-particles ($ZrO_2$-NPs) used in the Examples. The average diameter of the of zirconia nano-particles ($ZrO_2$-NPs) was found to be approximately 40 nm, e.g., at least 10, 12.5, 15, 17.5, 20, 25, 30, or 35 nm and/or up to 80, 75, 70, 65, 60, 55, 52.5, 50, 47.5, or 45 nm.

FIG. 1D show a transmission electron microscopy (TEM) image of the silver nano-particles (Ag-NPs) of the variety used in the Examples. FIG. 1E shows a selected area (electron) diffraction (SAD or SAED) TEM image of the silver nano-particles (Ag-NPs) used in the Examples. The electron diffraction patterns indicate a crystalline nature of the nano-particles, displaying near spherical shape. FIG. 1F shows a plot and chart of the particle size distribution of silver nano-particles (Ag-NPs) of the type used in the Examples. The average diameter of the silver nano-particles (Ag-NPs) was found to be approximately 20 nm, e.g., at least 1, 2, 3, 4, 5, 7.5, 10, 12.5, or 15 nm and/or up to 75, 65, 60, 55, 50, 45, 40, 35, 30, or 25 nm. The distribution of silver nano-particles (Ag-NPs) is generally flatter than that of the zirconia nano-particles ($ZrO_2$-NPs), i.e., the Ag-NPs are more disperse or less uniform in shape, having a higher standard deviation.

FIG. 2 shows schematic representations of the sample design in the study on the left panel, with suggested denture base with layers (right panel), with an upper row (A) illustrating a one-layer control having unmodified heat-polymerized acrylic resin (3), a middle row (B) illustration a Group I—one-layer sample made completely of modified heat-polymerized acrylic resin (4), and a lower row (C) illustrating a Group II—two-layer sample made of unmodified heat-polymerized acrylic resin (3) on a cameo surface (1) and lined with modified heat-polymerized acrylic resin (4) at the intaglio surface (2). The intaglio surface (2) is meant to refer to the surface appearing as a depression, i.e., into which the gums would press, though, in practice, the filled layer (4) may surround the intaglio surface and cover part or all of the cameo surface (1), whereby "cameo surface" (1) is meant to refer to the portion appearing as relief left remaining on the surface, e.g., from which unrequired material is chipped away in design, generally appearing raised or embossed on the surface. Typical filled-layer thicknesses in the two-layer samples are in a range of, e.g., at least 0.01, 0.025, 0.05, 0.075, 0.1, or 0.15 that of the filled layer and/or up to 0.67, 0.5, 0.45, 0.4, 0.35, 0.3, 0.25, 0.2, or 0.15 that of the filled layer. For example, the thickness of the filled layer may be, e.g., at least 0.1, 0.15, 0.2, 0.25, 0.3, 0.35, 0.4, 0.45, 0.5, 0.6, or 0.75 mm and/or up to 2, 1.75, 1.5, 1.25, 1.2, 1.1, 1, 0.95, 0.9, 0.85, 0.8, 0.75, 0.7, 0.65, 0.6, 0.55, or 0.5 mm.

FIG. 3 shows the results of Fourier-transform infrared (FTIR) analysis for pure poly(methyl methacrylate) PMMA (A), PMMA loaded with zirconia nano-particles ($ZrO_2$-NPs) (B), and PMMA loaded with silver nano-particles (Ag-NPs) (C). The FTIR spectra of the loaded samples showed similar bands and characteristic features to PMMA. The bands on the left shoulder at around 2920 $cm^{-1}$ can be attributed to $CH_3$ and $CH_2$ stretching vibration in the PMMA matrix. A sharp and intense band at ~1722 $cm^{-1}$ is attributable to carbonyl groups. The band at ~1144 $cm^{-1}$ indicates the C—O—C stretching vibrations of different modes. A band on the right shoulder at ~750 $cm^{-1}$ is attributable to a C—H out of plane deformation. The similar FTIR results for all the three samples indicates that the incorporation of nanofillers, zirconia nano-particles ($ZrO_2$-NPs) or silver nano-particles (Ag-NPs), into the PMMA matrix did not affect the structure of the PMMA chain.

Figure 4A:
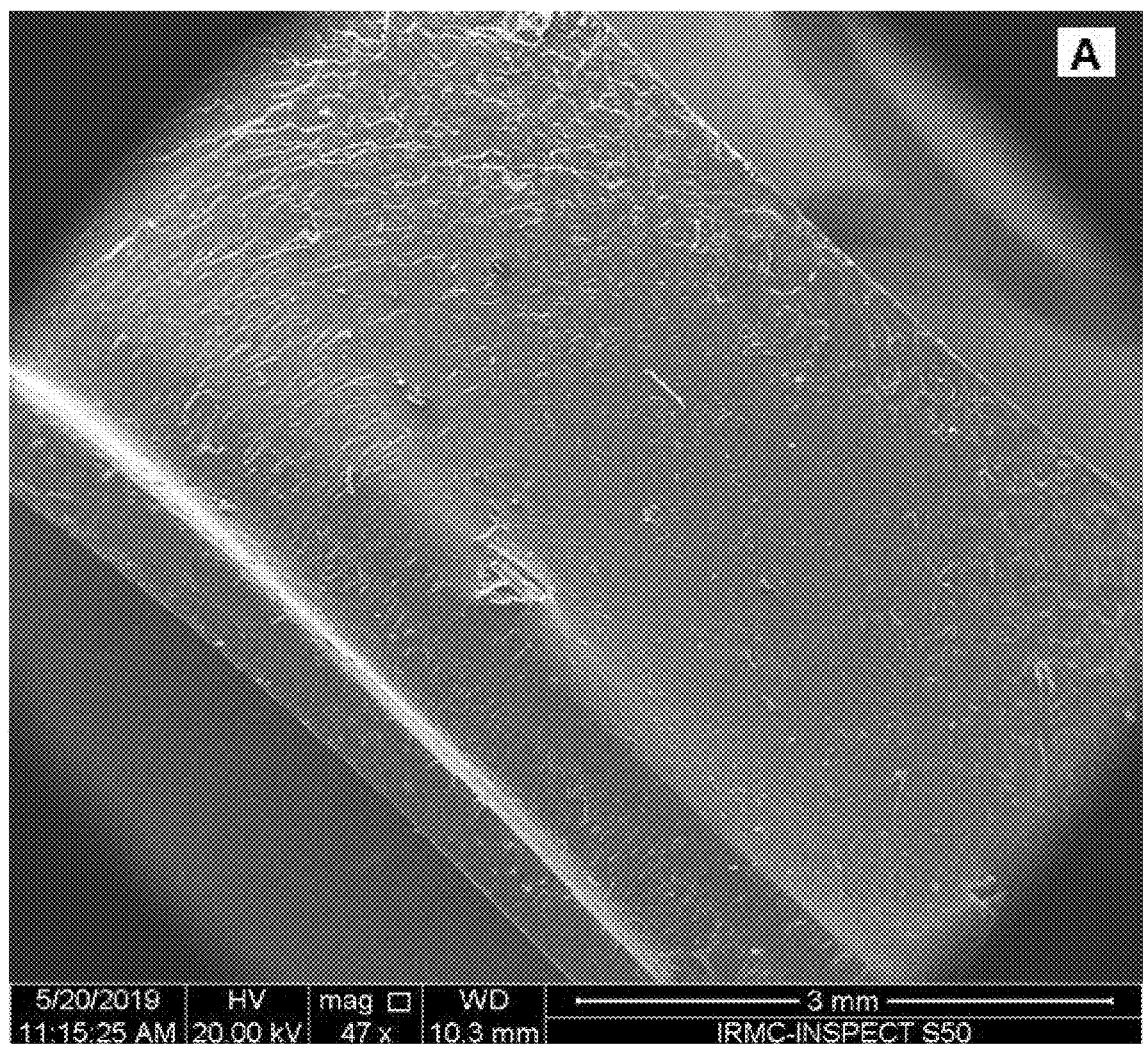
FIG. 4A shows a representative scanning electron microscope (SEM) image of the (intact) fracture surface of an unfilled, pure PMMA one-layer denture base material (control) at 3 mm magnification.
Figure 4B:
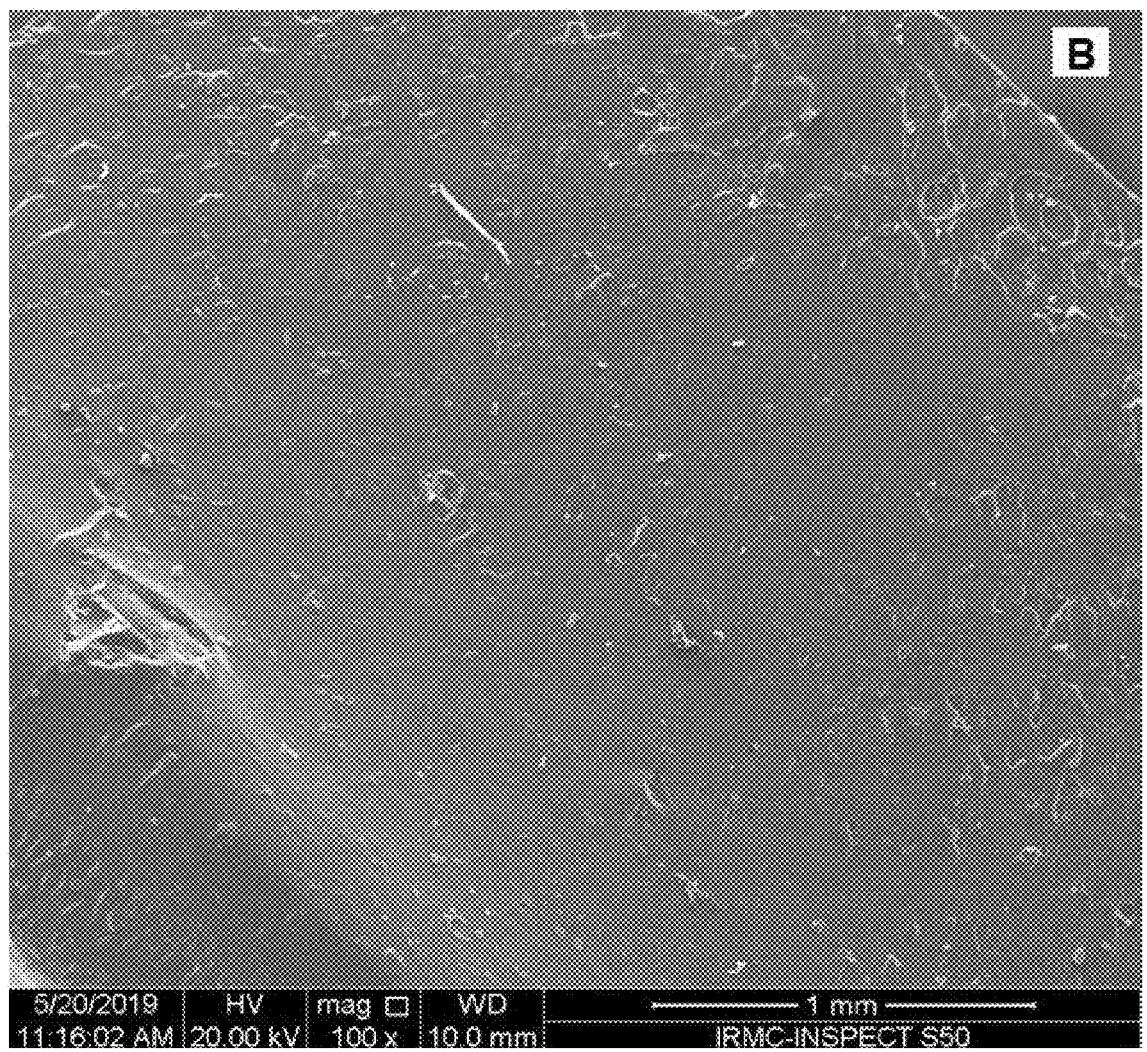
FIG. 4B shows a representative SEM image of the (intact) fracture surface of an unfilled, pure PMMA one-layer denture base material (control) at 1 mm magnification.
Figure 4C:
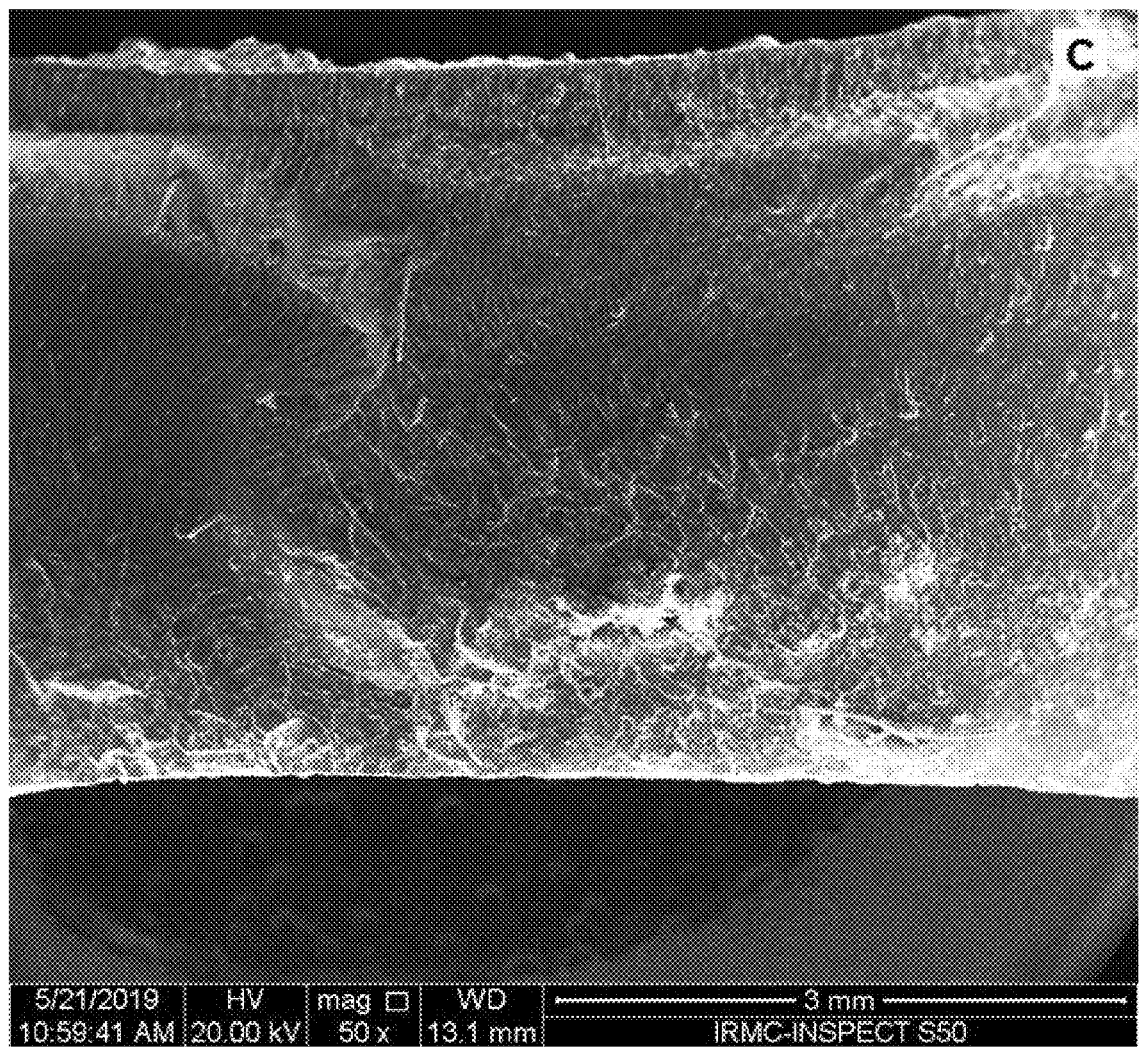
FIG. 4C shows a representative SEM image of the (intact) fracture surface of a one-layer PMMA denture base material including zirconia nano-particles ($ZrO_2$-NPs) at 3 mm magnification.
Figure 4D:
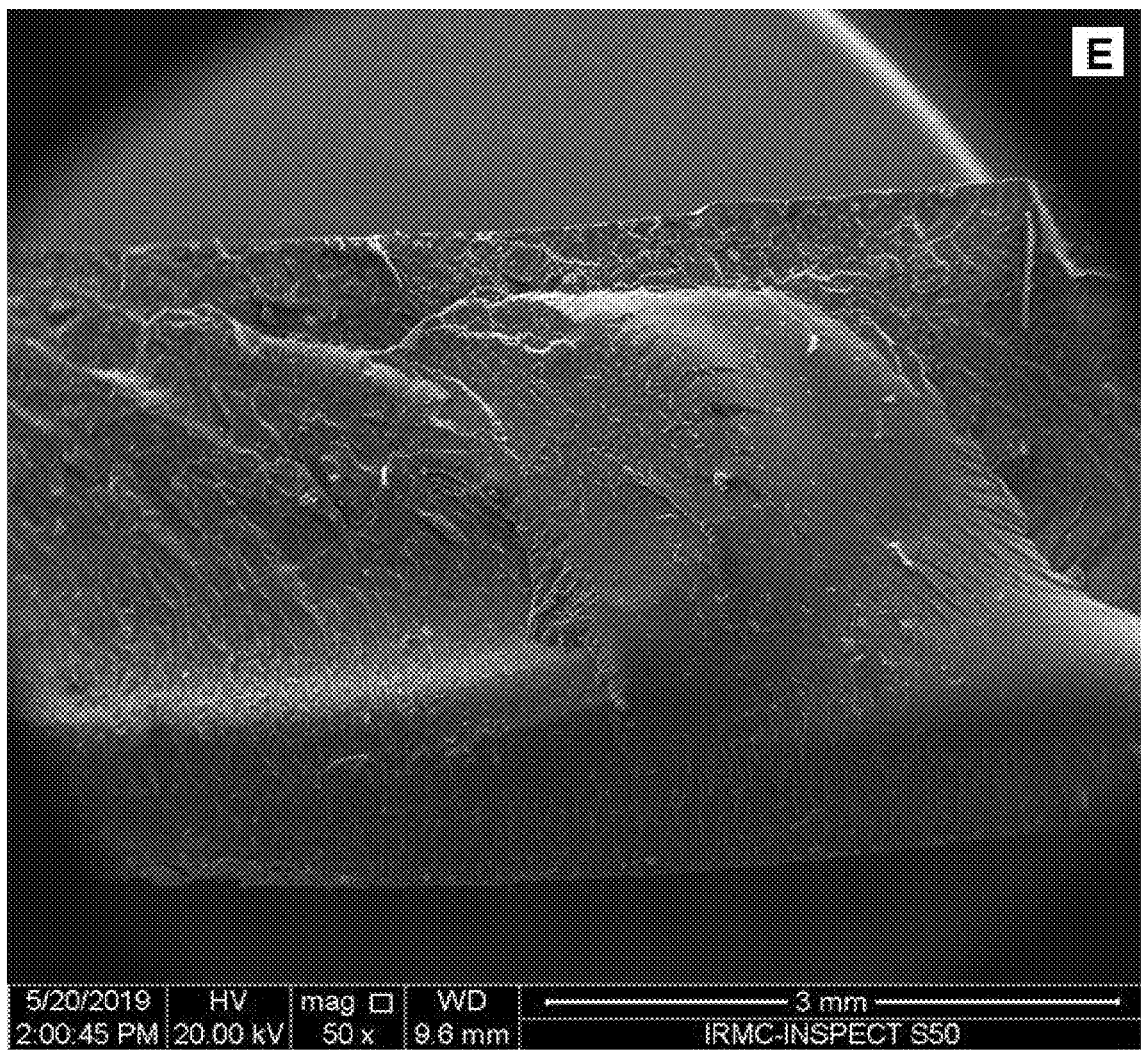
FIG. 4D shows a second representative SEM image of the (intact) fracture surface of a one-layer PMMA denture base material including zirconia nano-particles ($ZrO_2$-NPs) at 1 mm magnification.
Figure 4E:
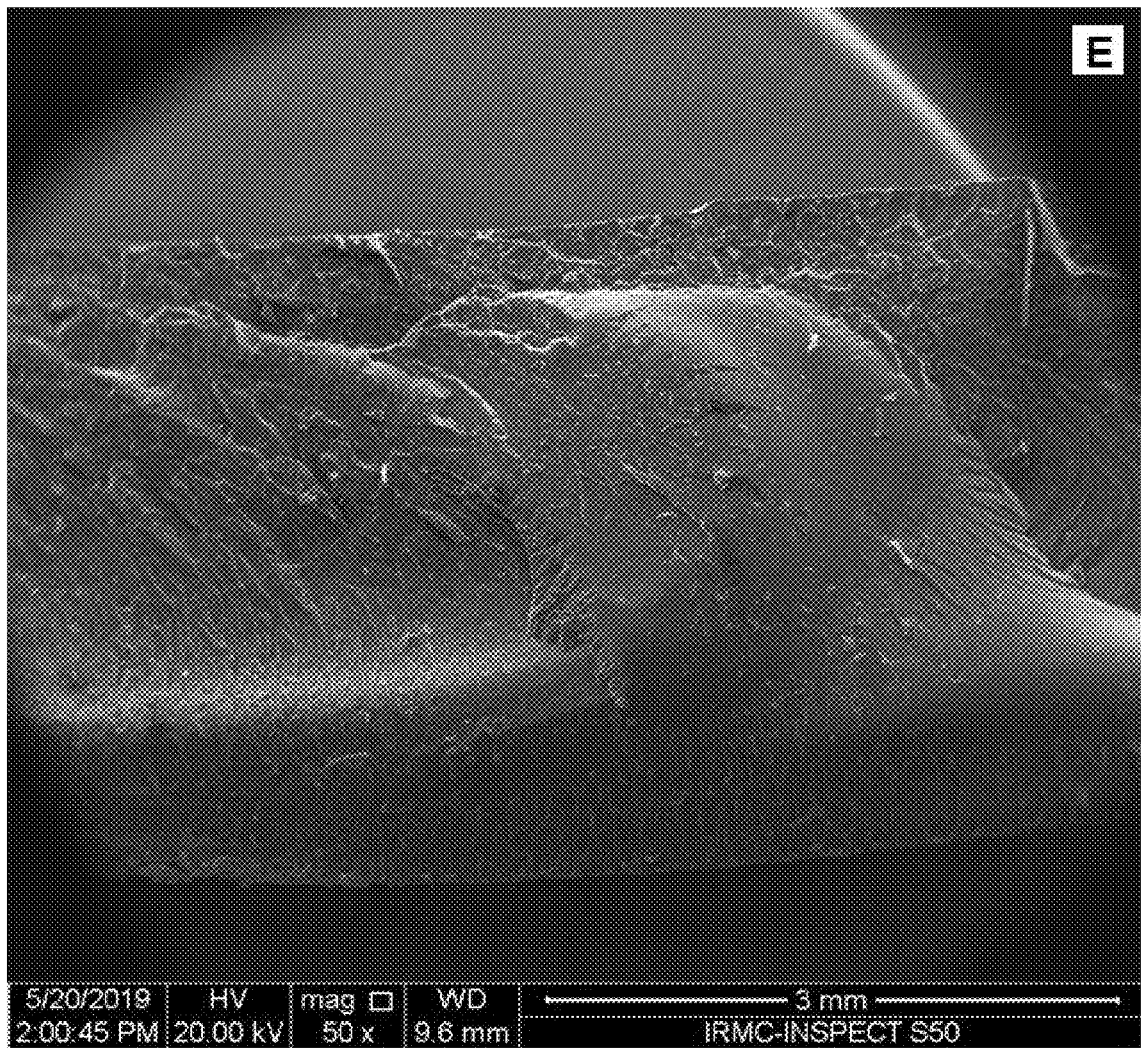
FIG. 4E shows a representative SEM image of the (intact) fracture surface of a one-layer PMMA denture base material including silver nano-particles (Ag-NPs) at 3 mm magnification.
Figure 4F:
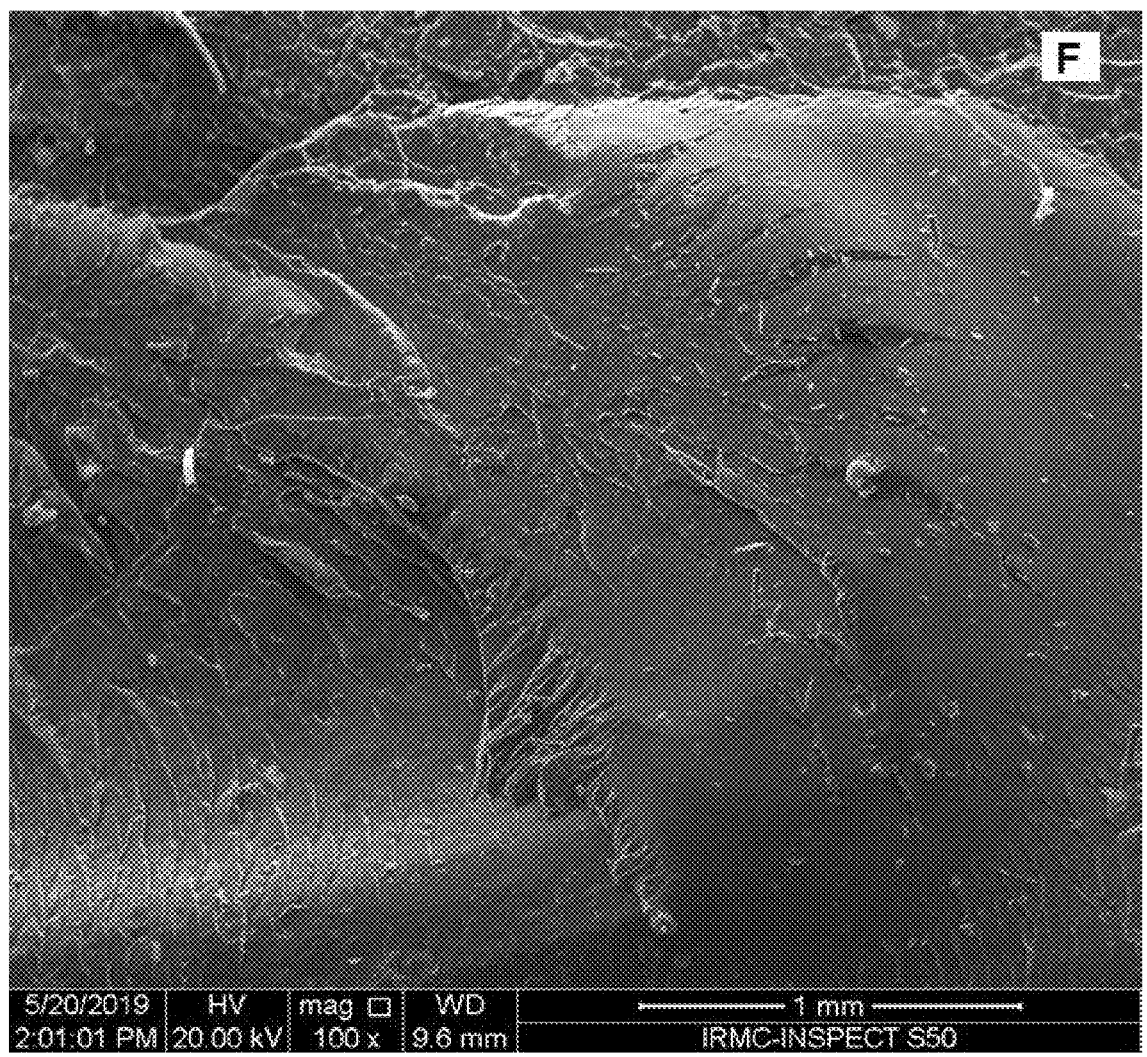
FIG. 4F shows a representative SEM image of the (intact) fracture surface of a one-layer PMMA denture base material including silver nano-particles (Ag-NPs) at 1 mm magnification.

FIG. 4A to 4D show scanning electron microscopy (SEM) images of samples from the Examples, including one-layer or two-layer denture base materials. FIGS. 4A and 4B, containing unmodified one-layer samples, showed a smooth surface from border to border, while the modified one-layer samples with zirconia nano-particles ($ZrO_2$-NPs) in FIGS. 4C and 4D and silver nano-particles (Ag-NPs) in FIGS. 4E and 4F, showed rough surfaces and similar characteristics throughout the fractured surface.

Figure 5A:
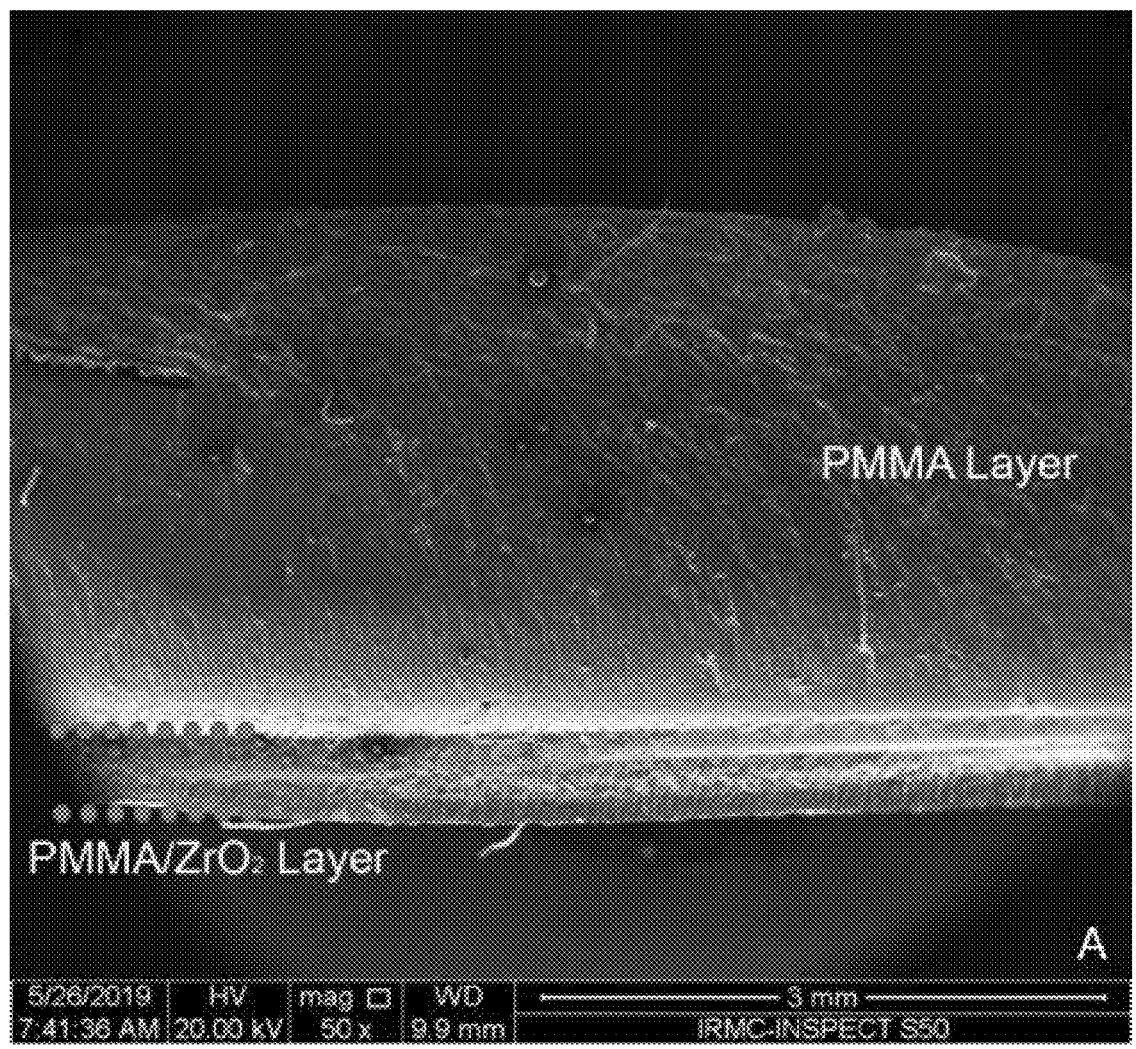
FIG. 5A shows a representative SEM images of the fractured surfaces showing two-layer PMMA denture base material including zirconia nano-particles (ZrO$_2$-NPs) at 1 mm magnification.
Figure 5B:
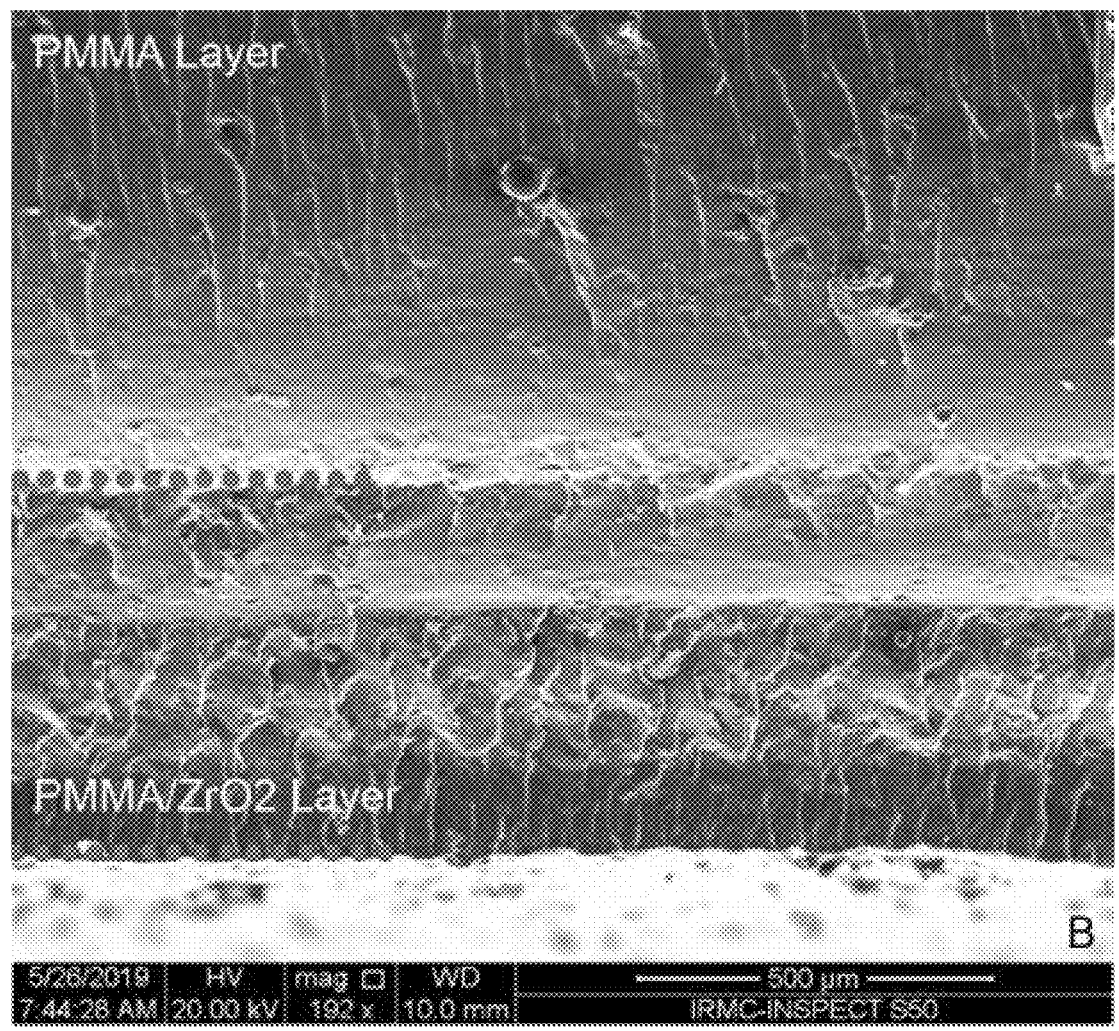
FIG. 5B shows a representative SEM images of the fractured surfaces showing two-layer PMMA denture base material including zirconia nano-particles (ZrO$_2$-NPs) at 500 μm magnification.
Figure 5C:
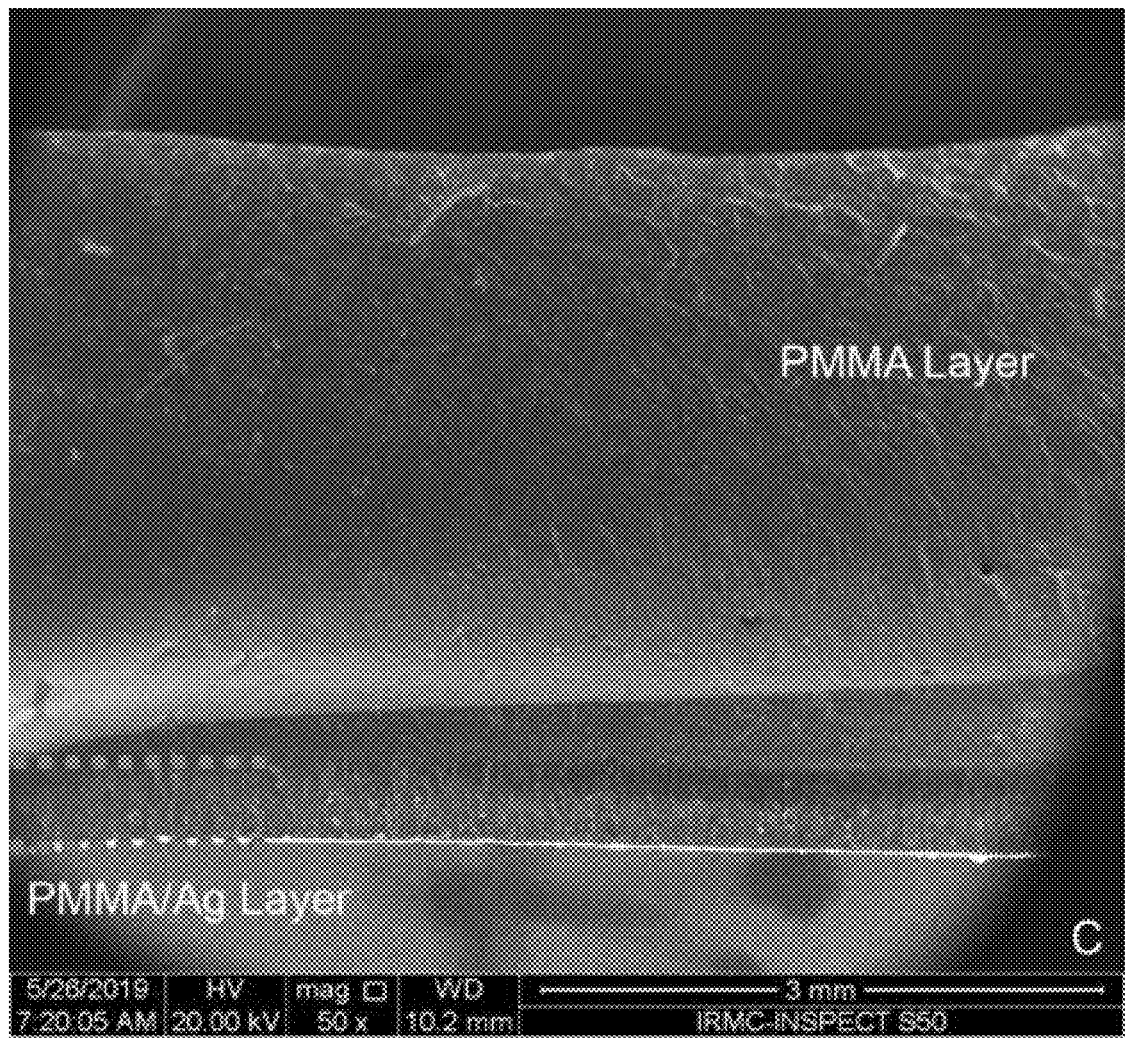
FIG. 5C shows a representative SEM images of the fractured surfaces showing two-layer PMMA denture base material including silver nano-particles (Ag-NPs) at 1 mm magnification.
Figure 5D:
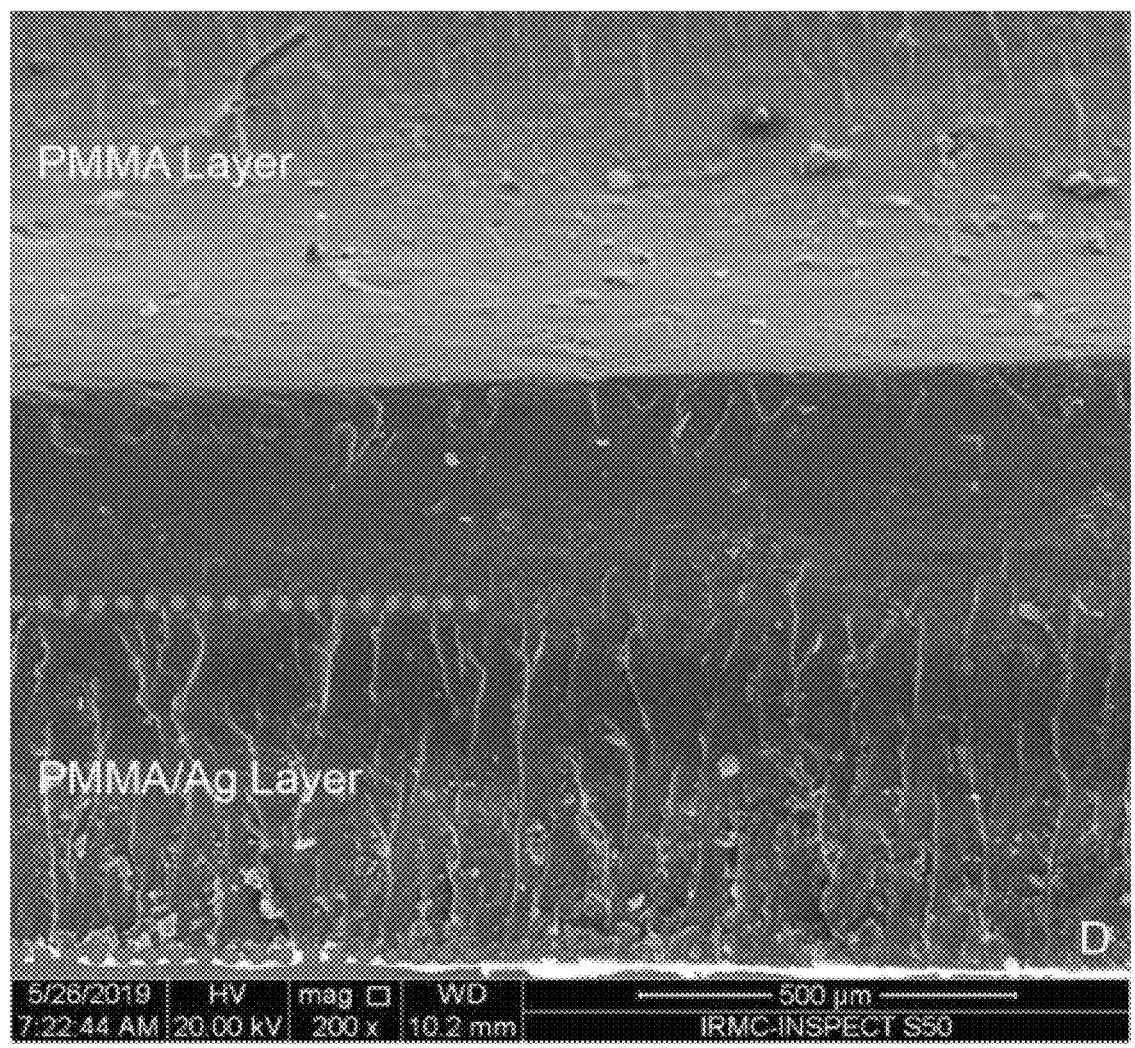
FIG. 5D shows a representative SEM images of the fractured surfaces showing two-layer PMMA denture base material including silver nano-particles (Ag-NPs) at 500 μm magnification.

FIG. 5A to 5D show SEM images including the features of two-layer samples having a distinct interface between the two layers evident for both types of nano-filler, i.e., zirconia nano-particles (ZrO$_2$-NPs) and silver nano-particles (Ag-NPs). FIGS. 5B and 5D show the modified layer in each sample, highlighted with red dashed lines and yellow arrows in high magnification images. The presence of nano-fillers and the nature of fracture collectively indicate the presence of two layers with average of 2.1 mm for the unmodified layer and 0.4 mm for the filler-modified layer. The filled layers may have, for example, vein-structures running parallel to a thickness direction, spaced by at least 10, 15, 20, 25, 30, 35, 40, 45, 50, 60, 67, 75, 85, 90, 95, 100, 110, 125, 133, or 150 µm and/or up to 250, 225, 200, 175, 150, 133, 125, 115, 110, 105, 100, 95, 90, 85, 80, or 75 µm.

Figure 6A:
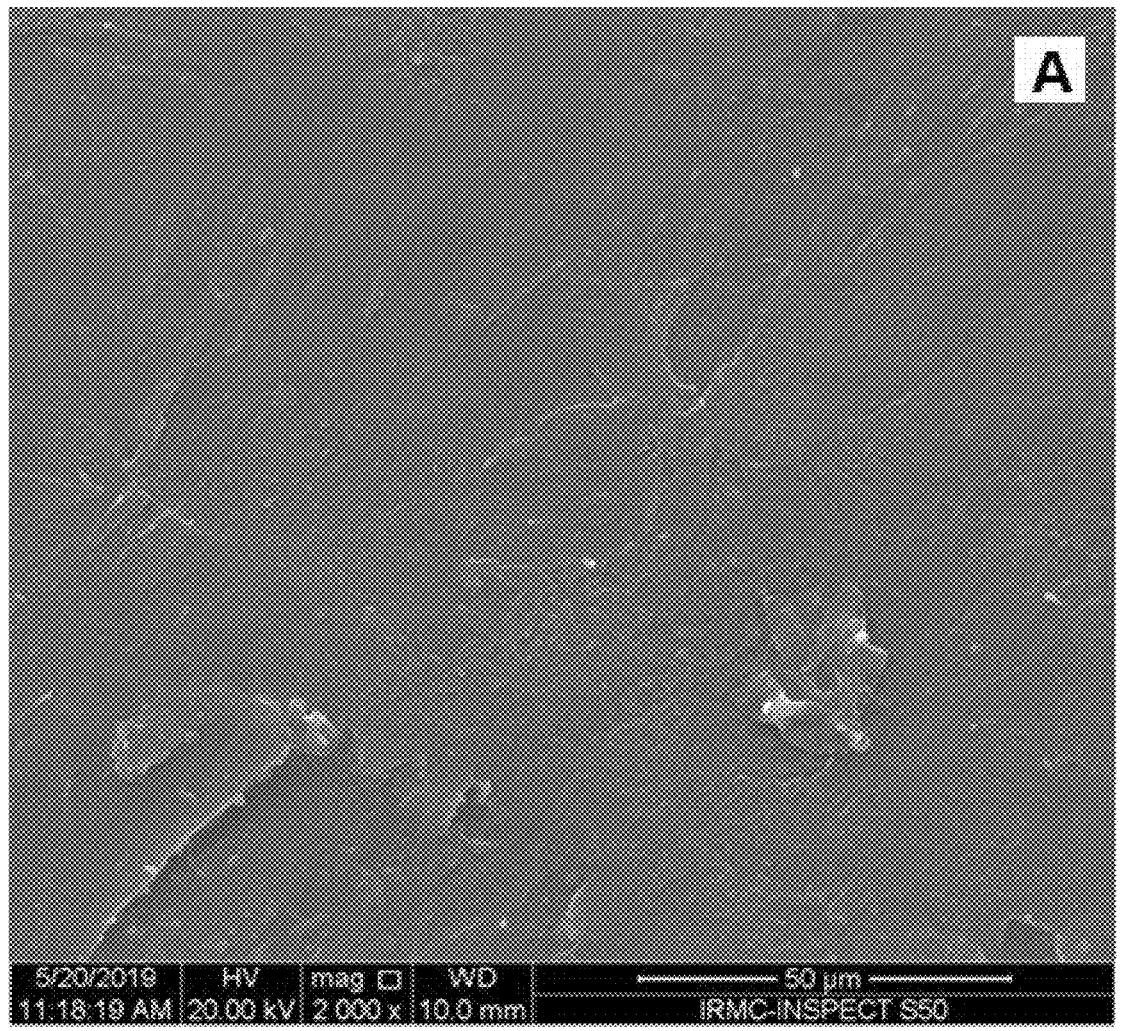
FIG. 6A shows a representative SEM image of the fractured surface of an unfilled, pure PMMA one-layer denture base material (control) at high magnification (×2000), i.e., 50 μm magnification.
Figure 6B:
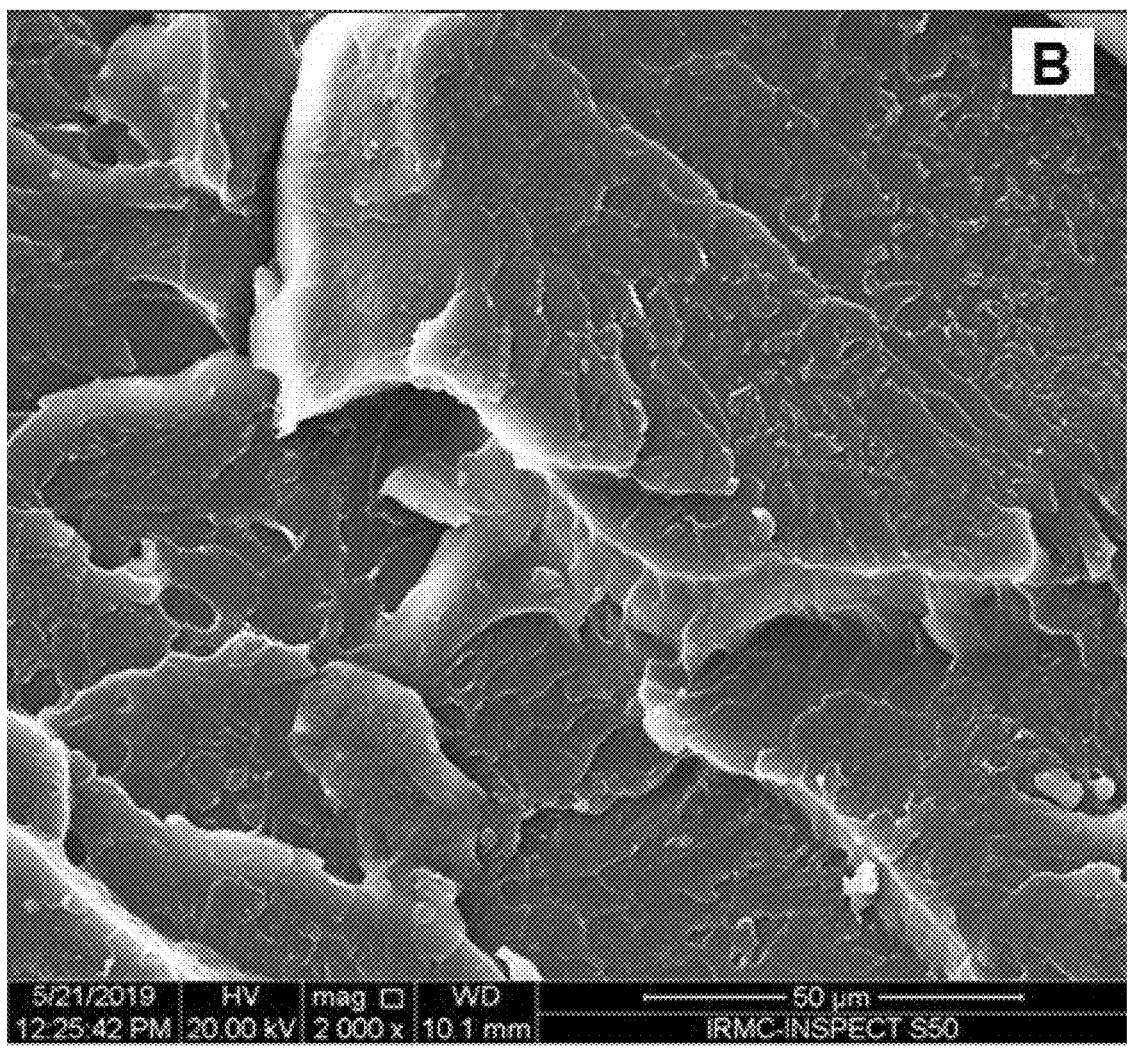
FIG. 6B shows a representative SEM image of the fractured surface of a two-layer PMMA denture base material filled with zirconia nano-particles (ZrO$_2$-NPs) at high magnification (×2000), i.e., 50 μm magnification.
Figure 6C:
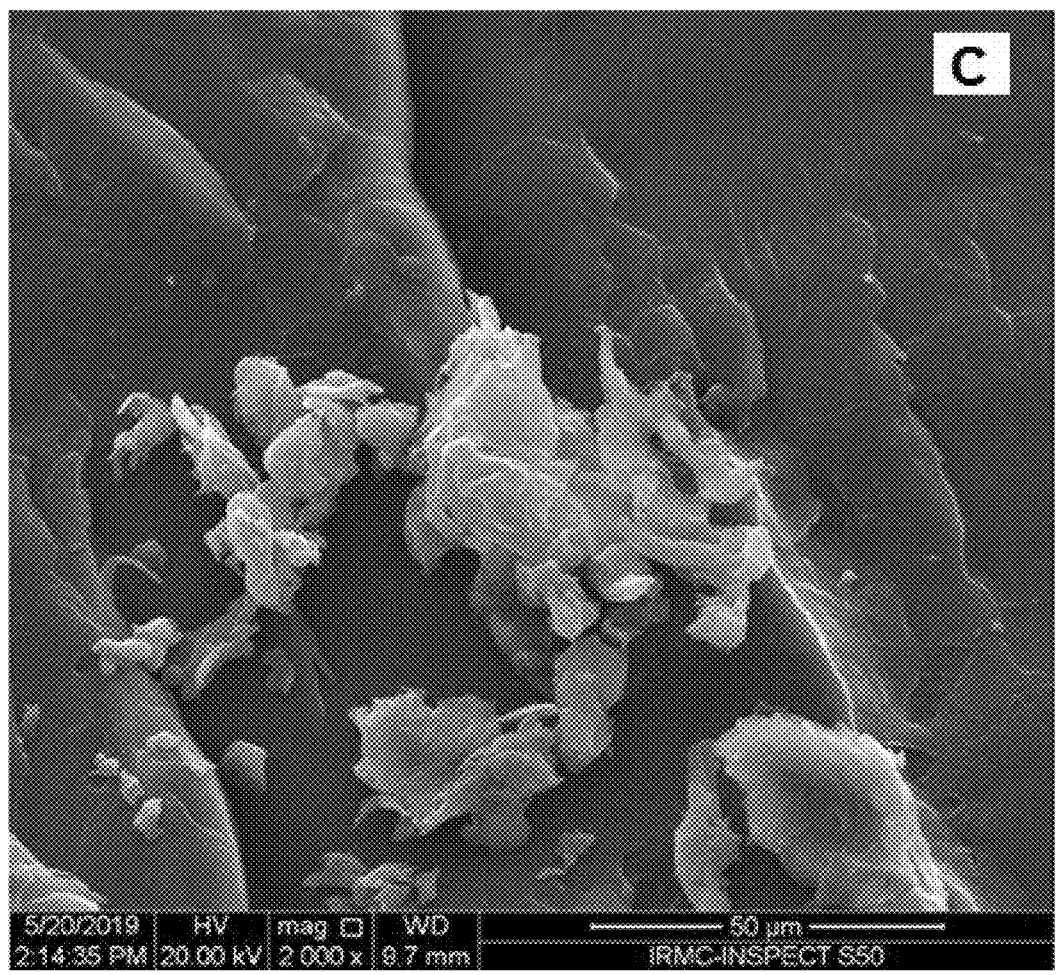
FIG. 6C shows a representative SEM image of the fractured surface of a two-layer PMMA denture base material filled with silver nano-particles (Ag-NPs) at high magnification (×2000), i.e., 50 μm magnification.

FIG. 6A to 6C include SEM images illustrating that the mode of failure was different according to the nano-filler type used in the sample. In the control samples shown in FIG. 6A, a smooth, mirror-like appearance, representing brittle fracture, was seen. A rougher surface, having trabeculae and step formation, with good distributions of zirconia nano-particles (ZrO$_2$-NPs) were seen on the zirconia-modified layer shown in FIG. 6B. For silver nano-particle (Ag-NP)-modified samples in FIG. 6C, slight changes in the surface topography were observable along with few cluster formations, representing a ductile mode of fracture for samples containing silver nano-particles (Ag-NPs).

Figure 7A:
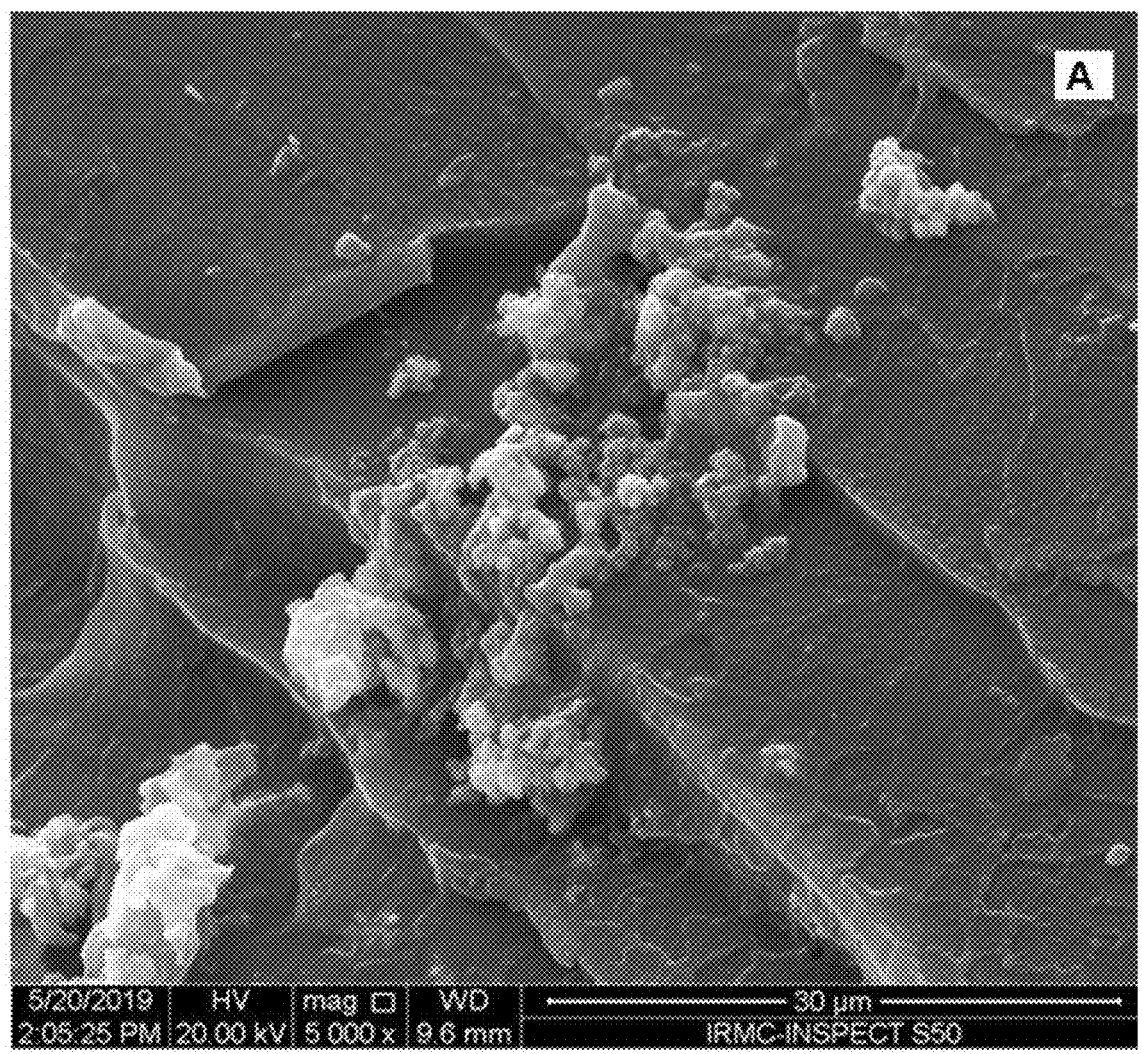
FIG. 7A shows an SEM image of the fractured surface of a two-layer PMMA denture base material filled with zirconia nano-particles (ZrO$_2$-NPs) at high magnification (×5000), i.e., 30 μm magnification, showing cluster formation.
Figure 7B:
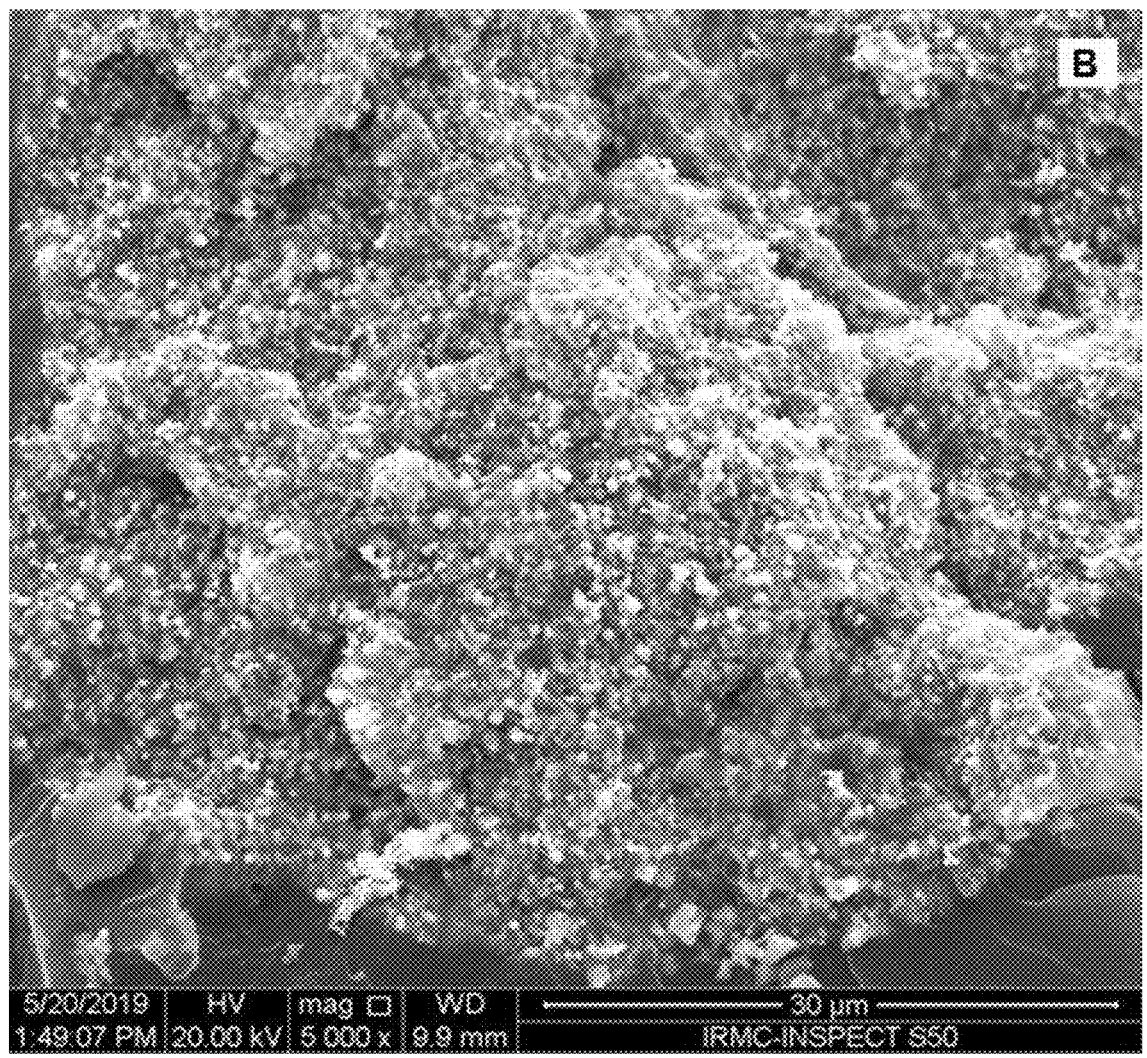
FIG. 7B shows an SEM image of the fractured surface of a two-layer PMMA denture base material filled with silver nano-particles (Ag-NPs) at high magnification (×5000), i.e., 30 μm magnification, showing cluster formation.

FIGS. 7A and 7B shows SEM images captured at high magnification displaying cluster formation of zirconia nano-particles (ZrO$_2$-NPs) in FIG. 7A and silver nano-particles (Ag-NPs) in FIG. 7B, which may have resulted in poor mechanical properties.

Numerous modifications and variations of the present invention are possible in light of the above teachings. It is therefore to be understood that within the scope of the appended claims, the invention may be practiced otherwise than as specifically described herein.

REFERENCE SIGNS

A one-layer conventional denture base material
B one-layer reinforced denture base material
C two-layer denture base material
1 cameo surface
2 intaglio surface
3 pure acrylic resin
4 modified acrylic resin

The invention claimed is:

1. A dental restoration base material, comprising:
a first layer comprising at least 90 wt. %, relative to total first layer weight, of a cured first composition comprising, prior to curing, a first (meth)acrylic polymer and a first (meth)acrylic monomer; and
a surface layer comprising at least 90 wt. %, relative to total surface layer weight, of a cured second composition comprising, prior to curing, a second (meth)acrylic polymer, a second (meth)acrylic monomer, and
0.45 to 0.55 wt. % of antimicrobial nanoparticles, relative to a total surface layer weight,
wherein no gradient in antimicrobial nanoparticle content and no continuous bulk containing the antimicrobial nanoparticles is present between the first and surface layers,
wherein the first layer is free of the antimicrobial nanoparticles,
wherein the antimicrobial nanoparticles are selected from silver nanoparticles and zirconium dioxide nanoparticles, and
wherein the material has a flexural strength in a range of 78 to 87 MPa, a translucency parameter in a range of 6.5 to 13, and a surface roughness in a range of 0.13 to 0.2 µm.

2. The material of claim 1, wherein the silver nanoparticles have an average particle size of 5 to 40 nm.

3. The material of claim 1, wherein the zirconium dioxide nanoparticles have an average particle size of 20 to 60 nm.

4. The material of claim 1, wherein the antimicrobial nanoparticles comprise no more than 0.1 wt. % organic compounds, relative to the total material weight.

5. The material of claim 1, wherein the surface layer directly contacts the first layer on at least portions of the first layer.

6. The material of claim 1, arranged such that, in operation, the surface layer is configured to contact oral fluids and to shield any layers below the surface layer, including the first layer, from the oral fluids.

7. The material of claim 1, wherein the surface layer has a thickness no more than 20% that of a total material thickness.

8. The material of claim 1, wherein the surface layer has a thickness of 100 to 3,000 µm.

9. The material of claim 1, wherein the first (meth)acrylic polymer and the second (meth)acrylic polymer each comprise at least 90 wt. % poly(methyl methacrylate).

10. The material of claim 1, wherein the first (meth)acrylic monomer and the second (meth)acrylic monomer each comprise at least 90 wt. % methyl methacrylate.

11. The material of claim 1, wherein the first (meth)acrylic polymer and the second (meth)acrylic polymer are the same, wherein the first (meth)acrylic monomer and the second (meth)acrylic monomer are the same, and
wherein the first and the second (meth)acrylic monomer are suitable to form the same polymer as the first and the second (meth)acrylic polymer.

12. The material of claim 1, which is suitable to reduce *Candida* adhesion to a dental prosthesis by at least 10%, relative to materials comprising the first layer alone.

13. A denture, comprising the material of claim 1.

14. A method of preventing or reducing adhesion of a microorganism to a dental restoration, the method comprising inserting into an oral cavity of a subject in need thereof the dental restoration comprising the material of claim 1; and maintaining the dental restoration in the oral cavity for at least 3 hours.

15. The method of claim 14, wherein the microorganism is a *Candida* species of fungus.

16. A method of making the dental restoration base material of claim 1, the method comprising:
prepolymerizing the first composition comprising the first (meth)acrylic monomer and the first (meth)acrylic polymer, to obtain a first viscous composition;
conforming the first viscous composition into a dental mold;
prepolymerizing the second composition comprising the second (meth)acrylic monomer, 0.45 to 0.55 wt. %, relative to a total second composition weight, of the antimicrobial nanoparticles, and the second (meth)acrylic polymer, to obtain a second viscous composition;
conforming the second viscous composition into the dental mold over the first viscous composition;
polymerizing the first and second viscous compositions in the dental mold, thereby forming the dental restoration base material.

17. The material of claim 1, wherein the surface layer comprises about 0.5 wt. % of the antimicrobial nanoparticles, relative to a total surface layer weight.

18. A dental restoration base material, comprising:
a first layer comprising at least 90 wt. %, relative to total first layer weight, of a cured first composition comprising, prior to curing, a first (meth)acrylic polymer and a first (meth)acrylic monomer; and
a surface layer comprising at least 90 wt. %, relative to total surface layer weight, of a cured second composition comprising, prior to curing, a second (meth)acrylic polymer, a second (meth)acrylic monomer, and
0.5 wt. % of silver nanoparticles, relative to a total surface layer weight, wherein no gradient in silver nanoparticles content and no continuous bulk containing the silver nanoparticles is present between the first and surface layers,
wherein the first layer is free of the silver nanoparticles, and
wherein the material has a flexural strength in a range of 78 to 82 MPa, a translucency parameter in a range of 6.5 to 7.5, and a surface roughness in a range of 0.18 to 0.2 μm.

19. A dental restoration base material, comprising:
a first layer comprising at least 90 wt. %, relative to total first layer weight, of a cured first composition comprising, prior to curing, a first (meth)acrylic polymer and a first (meth)acrylic monomer; and
a surface layer comprising at least 90 wt. %, relative to total surface layer weight, of a cured second composition comprising, prior to curing, a second (meth)acrylic polymer, a second (meth)acrylic monomer, and
0.5 wt. % of zirconium dioxide nanoparticles, relative to a total surface layer weight, wherein no gradient in zirconium dioxide nanoparticles content and no continuous bulk containing the zirconium dioxide nanoparticles is present between the first and surface layers,
wherein the first layer is free of the zirconium dioxide nanoparticles, and
wherein the material has a flexural strength in a range of 85 to 87 MPa, a translucency parameter in a range of 12 to 13, and a surface roughness in a range of 0.13 to 0.15 μm.

* * * * *